United States Patent
Saxena et al.

(10) Patent No.: US 9,459,378 B2
(45) Date of Patent: Oct. 4, 2016

(54) HYDROPHILIC SILICONE MONOMERS, PROCESS FOR PREPARATION THEREOF AND THIN FILMS CONTAINING THE SAME

(71) Applicants: Anubhav Saxena, Bangalore (IN); Shreedhar Bhat, Bangalore (IN); Senthilkumar Umapathy, Bangalore (IN); Kenrick M. Lewis, Flushing, NY (US)

(72) Inventors: Anubhav Saxena, Bangalore (IN); Shreedhar Bhat, Bangalore (IN); Senthilkumar Umapathy, Bangalore (IN); Kenrick M. Lewis, Flushing, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 79 days.

(21) Appl. No.: 14/492,489

(22) Filed: Sep. 22, 2014

(65) Prior Publication Data

US 2015/0011661 A1    Jan. 8, 2015

Related U.S. Application Data

(63) Continuation of application No. PCT/US2013/029345, filed on Mar. 6, 2013.

(60) Provisional application No. 61/614,243, filed on Mar. 22, 2012.

(51) Int. Cl.

| | |
|---|---|
| *G02B 1/04* | (2006.01) |
| *A61K 8/81* | (2006.01) |
| *A61Q 5/02* | (2006.01) |
| *C09D 143/04* | (2006.01) |
| *D21H 17/59* | (2006.01) |
| *C08F 230/08* | (2006.01) |
| *C08G 77/388* | (2006.01) |
| *C08G 77/46* | (2006.01) |
| *D06M 15/643* | (2006.01) |
| *C08G 77/20* | (2006.01) |

(52) U.S. Cl.
CPC ............ *G02B 1/043* (2013.01); *A61K 8/8158* (2013.01); *A61Q 5/02* (2013.01); *C08F 230/08* (2013.01); *C08G 77/388* (2013.01); *C08G 77/46* (2013.01); *C09D 143/04* (2013.01); *D06M 15/643* (2013.01); *D06M 15/6436* (2013.01); *D21H 17/59* (2013.01); *A61K 2800/10* (2013.01); *C08G 77/20* (2013.01); *D06M 2200/50* (2013.01)

(58) Field of Classification Search
CPC .. G02B 1/043; A61K 8/8158; C09D 143/04; A61Q 5/02; D21H 17/59; D06M 15/643; D06M 15/6436; C08F 230/08; C08G 77/46; C08G 77/388

USPC .............. 514/785, 788; 510/466; 522/64; 524/547; 523/107; 252/182.14, 183.11
See application file for complete search history.

(56) References Cited

U.S. PATENT DOCUMENTS

| | | |
|---|---|---|
| 3,299,112 A | 1/1967 | Bailey |
| 3,408,429 A | 10/1968 | Wichterle |
| 3,496,254 A | 2/1970 | Wichterle |
| 3,507,923 A | 4/1970 | Gessner et al. |
| 4,084,459 A | 4/1978 | Clark |
| 4,150,048 A | 4/1979 | Schilling, Jr. et al. |
| 4,197,266 A | 4/1980 | Clark et al. |
| 4,260,725 A | 4/1981 | Keogh et al. |
| 4,847,398 A | 7/1989 | Mehta et al. |
| 4,857,583 A | 8/1989 | Austin et al. |
| 5,159,096 A | 10/1992 | Austin et al. |
| 5,191,103 A | 3/1993 | Mehta et al. |
| 5,352,714 A | 10/1994 | Lai et al. |
| 5,986,122 A | 11/1999 | Lewis et al. |
| 5,998,498 A | 12/1999 | Vanderlaan et al. |
| 6,013,711 A | 1/2000 | Lewis et al. |
| 6,207,782 B1 | 3/2001 | Czech et al. |
| 6,867,245 B2 | 3/2005 | Iwata et al. |
| 2010/0258961 A1 | 10/2010 | Chang et al. |
| 2011/0181833 A1* | 7/2011 | Guyer ............... C07F 7/0852 351/159.33 |

FOREIGN PATENT DOCUMENTS

| | | |
|---|---|---|
| WO | 01/46717 A1 | 6/2001 |
| WO | 2010/038242 A2 | 4/2010 |

OTHER PUBLICATIONS

Patent Cooperation Treaty (PCT), International Search Report and Written Opinion for Application PCT/US13/29345 filed Mar. 6, 2013, mailed May 20, 2013, 9 pp., International Searching Authority, US.

Extended European Search Report for Application EP13763709.6, PCT/US2013/029345, dated Sep. 30, 2015, 6 pp., European Patent Office, Germany.

* cited by examiner

*Primary Examiner* — Porfirio Nazario Gonzalez
(74) *Attorney, Agent, or Firm* — Joseph Ostroff; McDonald Hopkins LLC

(57) ABSTRACT

The present invention relates to a fast curing compositions comprising a (meth)acrylamide functionalized hydrophilic silicone monomers having a polyether moiety containing a branched linking group. In one embodiment, such compositions are useful for preparing water-absorbing silicone-hydrogel films for contact lens applications. In one embodiment, the (meth)acrylamide monomers disclosed here have a branched linking group on the polyether moiety which makes it possible to produce hydrophilic polyether modified silicone copolymers without the need to separate various by-products including, but not limited to, unreacted, isomerized polyether and associated high molecular weight by-products.

22 Claims, No Drawings

HYDROPHILIC SILICONE MONOMERS, PROCESS FOR PREPARATION THEREOF AND THIN FILMS CONTAINING THE SAME

CROSS REFERENCE TO RELATED APPLICATIONS

This application is a continuation of International Patent Application No. PCT/US2013/029345, entitled "Hydrophilic Silicone Monomers, Process For Preparation Thereof And Thin Films Containing The Same", filed on Mar. 6, 2013, which claims the priority benefit of U.S. Provisional Patent No. 61/614,243 entitled "Hydrophilic Silicone Monomers, Process For Preparation Thereof And Thin Films Containing The Same", filed on Mar. 22, 2012, each of which are hereby incorporated in their entirety by reference.

FIELD OF THE INVENTION

The present invention relates to a fast curing composition comprising a (meth)acrylamide functionalized hydrophilic silicone monomer having a polyether moiety containing a branched linking group. In one embodiment, such compositions are useful for preparing water-absorbing silicone-hydrogel films for contact lens applications. In one embodiment, the (meth)acrylamide monomers disclosed here have a branched linking group on the polyether moiety, which makes it possible to produce hydrophilic polyether modified silicone copolymers without the need to separate various by-products including, but not limited to, unreacted, isomerized polyether and associated high molecular weight by-products.

BACKGROUND OF THE INVENTION

Silicone-hydrogel films are used to make extended wear soft contact lenses due to oxygen permeability, flexibility, comfort and reduced corneal complications. Conventional hydrogel materials (e.g., 2-hydroxyethylmethacrylate, HEMA) by themselves have poor oxygen permeability and they transport oxygen to the eye through the absorbed water molecules. Water has low oxygen permeability, also called the Dk value, which can be expressed in Barrer, wherein 1 Barrer=$10^{-11}$ (cm$^3$ O$_2$) cm cm$^{-2}$ s$^{-1}$ mmHg$^{-1}$ where "cm$^3$ O$_2$" is at a quantity of oxygen at standard temperature and pressure and where 'cm' represents the thickness of the material and cm$^{-2}$ is the reciprocal of the surface area of that material. The Dk of water is 80 Barrer. These lenses upon exposure to atmospheric air for longer periods are slowly dehydrated and the amount of oxygen transported to the cornea is reduced with time. Eye irritation, redness and other corneal complications can result and hence restrict use of the lenses to limited periods of wear.

Silicone-hydrogels with the comfort of soft contact lenses and significantly higher oxygen permeability overcame the obstacles for periods of wear beyond conventional hydrogels and were revolutionary in the field of optometry. The following patents describe silicone-hydrogels for use in contact lenses.

U.S. Pat. No. 4,260,725, assigned to Bausch & Lomb Inc., describes a water absorbing, soft, hydrophilic, flexible, hydrolytically stable, biologically inert contact lens with the capability of transporting oxygen sufficiently to meet the requirements of the human cornea comprising a polysiloxane which is α,ω terminally bonded through divalent hydrocarbon groups to polymerizably activated unsaturated groups and which contain hydrophilic side chains.

U.S. Pat. No. 5,352,714, assigned to Bausch & Lomb Inc., describes silicone-containing hydrogels with enhanced wettability comprising a silicone-containing monomer, hydrophilic monomers, and a relatively non-polar ring-containing monomer able to be converted to a highly polar amino acid upon hydration.

U.S. Pat. No. 5,998,498, assigned to Johnson & Johnson Vision Products, describes a silicone hydrogel prepared by curing a reaction mixture comprising a silicone-containing monomer having the following structure:

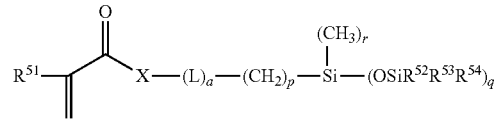

wherein $R^{51}$ is H or CH$_3$, q is for 2 and for each q, $R^{52}$, $R^{53}$ and $R^{54}$ are independently ethyl, methyl, benzyl, phenyl or a monovalent siloxane chain comprising from 1 to 100 repeating Si—O units, p is 1 to 10, r=(3-q), X is O or NR$^{55}$, where R$^{55}$ is H or a monovalent alkyl group with 1 to 4 carbons, a is 0 or 1, and L is a divalent linking group which in one embodiment comprises from 2 to 5 carbons, which can also optionally comprise ether or hydroxyl groups, for example, a polyethylene glycol chain.

U.S. Pat. No. 6,013,711, assigned to the CK Witco Corporation, describes a method for improving the miscibility of the lower molecular weight unsaturated siloxane—polyether copolymers with the α,ω-divinylpolysiloxanes without loss of storage stability, or delay of cure at the vulcanization temperature, or loss of permanent hydrophilicity or other desirable features of the cured polysiloxane. The compositions comprise one or more α,ω-divinylpolysiloxanes, unsaturated polysiloxane-polyether copolymers having from 2 to 5 silicon atoms per molecule, which in one embodiment are trisiloxanes, and a compatibilizing additive. The permanently hydrophilic, rapidly wettable polysiloxane compositions yield static water contact angles less than 50 degrees and dynamic advancing contact angles of less than about 100 degrees.

U.S. Pat. No. 6,207,782, assigned to Crompton Corporation, discloses acrylated hydrophilic polysiloxanes monomers and polymers and their copolymers with acrylate/methacrylate co-monomers and their emulsions for personal care, textile and coating applications. The acrylated siloxanes are represented by Formula (a):

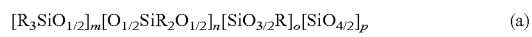

wherein R is selected from $R^1$ and P, wherein each $R^1$ can be the same or different and each is a monovalent hydrocarbon group; each P is $R^3[O(C_bH_{2b}O)_zCOCR^4=CH_2]_g$ wherein, $R^3$ is a polyvalent organic moiety, which can be hydroxy substituted alkylene, g is the valence of $R^3$ minus 1, $R^4$ is hydrogen or methyl; b=2 to 4, or even 2 to 3; z=1 to 1000, or even 3 to 30; and m+n+p+o=1 to 100, or even 2 to 20, at least one R is P; n=1 to 100; when o is not zero the ratio of n/o is less than 10:1; when p is not zero the ratio of n/p is less than 10:1; and m=0 to 10. A suitable, non-limiting example of an acrylated siloxane of the present invention is of the Formula (b):

wherein x and y can be 0 or an integer, or each x and y are from 0 to 100, or even from 0 to 25; Q can be R' or P, with the proviso that the average acrylate functionality is greater than 1 unsaturated groups per molecule. In one embodiment y=0 and Q=P.

U.S. Pat. No. 6,867,245, assigned to Asahikasei Aime Co., describes a soft contact lens, and provides a contact lens which shows small and stable contact angle to water at its surface in water as well as in air, little deposition in wearing, high oxygen permeability, no adhesion of lens to a cornea and superior extended-wearing characteristics. It describes a hydrogel soft contact lens, which has contact angle at a lens surface in a range of 10 to 50 degrees by the captive bubble method in water and 3 and 90 degrees by the sessile drop method in air, oxygen permeability of not less than 30 Dk and water content of not less than 5 percent, and also a hydrogel soft contact lens consisting of a polymer comprising a hydrophilic siloxanyl monomer shown by a specified general formula. This patent discloses copolymers of hydrophilic siloxane with amide-group containing monomers that are stated as being useful materials for contact lenses. The polymer comprises hydrophilic amide-group containing siloxanyl methacrylate, a siloxanyl methacrylate (3-tris [trimethylsiloxy]silylpropylmethacrylate, abbreviated as TRIS) including a hydrophilic polyether modified siloxanyl alkyl methacrylate and a cross-linkable monomer.

Various silicone polyethers are typically produced by hydrosilylation reactions of silanic hydrogen containing siloxanes with polyethers containing primary olefinic groups. However, in the event the olefinic groups do not have branching at the β-position, there is a possibility of isomerization of the double bond making it ineffective. Therefore, in such cases use of excess moles of polyethers are required that cannot be separated easily, and, moreover, the excess polyether can increase the modulus of the resulting lens making it less flexible.

Published PCT Patent Application No. WO 2010/038242 assigned to Momentive Performance Materials Inc., USA, discloses hydrophilic mono-functional silicone containing monomers with the Formula below:

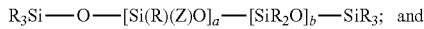

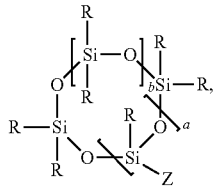

wherein a is 1 to 50; b is 0 to 100; each R is independently selected from the group consisting of monovalent aliphatic, cycloaliphatic or aromatic hydrocarbon groups of 1 to about 10 carbons and halogenated hydrocarbon groups of 1 to about 10 carbons, and Z is a polyether moiety having a branched alkyl group having the following Formula:

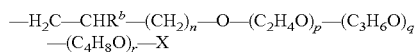

wherein n is 1 to about 20; p and q are independently 0 to about 100; r is 0 to about 50 and (p+q+r) is greater than 0; $R^b$ is an alkyl group having from 1 to about 4 carbon atoms, X is a polyether-capping group having the following Formula:

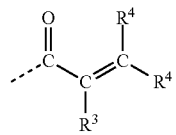

wherein $R^3$ and $R^4$ independently are either hydrogen or a substituted or unsubstituted saturated monovalent hydrocarbon group of 1 to about 20 carbons or —COOH or —CH$_2$—COOH.

Conventionally, silicone-hydrogels are made by polymerizing the acrylate or methacrylate functionalized silicone monomer with hydrogel (hydrophilic) monomers, such as hydroxyethyl methacrylate (HEMA), N-Vinylpyrrolidone (NVP) and other monomers such as methyl methacrylic acid (MAA), dimethylacrylamide (DMA), etc, in the presence of cross-linker and free radical or photoinitiators. Cross-linking agents generally have two or more reactive functional groups at different sites of the molecule. Typically, these sites contain polymerizable ethylenic unsaturation groups. During curing, they form a covalent bond with two different polymer chains and form a stable three-dimensional network to improve the strength of the polymer. Cross-linking agents conventionally used in contact lenses include ethylene glycol dimethacrylate and trimethyloylpropane trimethacrylate (about 0.1 to 2 weight percent). Other useful cross-linking agents include diethyleneglycol dimethacrylate, bisphenol A dimethacrylate, diglycidyl bisphenol A dimethacrylate and dimethacrylate-terminated polyethylene glycol and reactive linear polyether modified silicones.

Generally, silicone hydrogel contact lens materials are made using either hydrophobic mono-functional silicone monomer (such as TRIS) or multi-functional hydrophilic silicone monomer followed by secondary surface treatment. Mono-functional silicone monomers are preferred in the contact lens industry over multi-functional silicone monomers since the latter lead to increased rigidity of the lens made there from.

Although the state of this art for soft contact lenses has been improving, the silicone-based materials described in these patents still possess major shortfalls, like sub-optimal surface wettability and lipid deposition. In an effort to overcome these drawbacks, current state of the art technology uses either expensive secondary surface treatments called "plasma oxidation" or use internal wetting agents at the expense of oxygen permeability. Hence, there remains a need for hydrophilic silicone monomers with advantageous wettability and oxygen permeability that can be used to make contact lenses without the drawbacks and expensive surface treatments necessary with the silicone containing materials of the present art.

Hydrosilylation synthesis of siloxane-polyether copolymers with alkyl branched unsaturated polyethers, such as methylallyl polyethers, is known in the art. See for example, U.S. Pat. No. 3,507,923 and U.S. Pat. No. 4,150,048. However, the realization of improved oxygen permeability and water wettability in polymer films prepared from acrylate and methacrylate capped derivatives of these siloxane-polyether copolymers is novel. It is also an issue that structures with acrylamide pendant groups are more difficult to synthesize and thus cannot be produce via synthesis routes utilized to produce various silicone-hydrogel compositions having acrylate pendant groups.

SUMMARY OF THE INVENTION

The present invention provides new mono-acrylate or methacrylate functionalized silicone monomers containing a polyether moiety with a branched linking group, processes to produce such monomers with high purity and ease of manufacturability and homo and copolymers made from these monomers that have greater hydrophilic functionality. These functionalized silicone monomers are useful to make water-absorbing, oxygen-permeable silicone-hydrogel films that can be fashioned into extended wear soft contact lens. In particular, the monomers disclosed in the current invention have a branched linking group, which connects the siloxane unit with the polyalkyleneoxide block terminally functionalized with a reactive methacrylate group. Silicone hydrogel films produced with these monomers offer improved surface wettability, oxygen permeability and mechanical properties in comparison to silicone-hydrogel films prepared from monomers having linear alkyl linking groups, such as those already disclosed in the prior art for contact lens applications.

The present invention relates, in one aspect, to a fast curing composition comprising a (meth)acrylamide functionalized hydrophilic silicone monomer having a polyether moiety containing a branched linking group. In one embodiment, such compositions are useful for preparing water-absorbing silicone-hydrogel films for contact lens applications. In one embodiment, the (meth)acrylamide monomers in accordance with aspects of the invention have a branched linking group on the polyether moiety which makes it possible to produce hydrophilic polyether modified silicone copolymers without the need to separate various by-products including, but not limited to, unreacted, isomerized polyether and associated high molecular weight by-products.

In one embodiment, the present invention relates to hydrogel compositions and methods of making same. In one embodiment, the present invention comprises a silicone containing (meth)acrylamide polyethyleneoxide copolymer formed from the reaction product of free-radical polymerizable siloxane monomers such as TRIS, free-radical polymerizable organic monomers, at least one initiator and, optionally, at least one cross-linking compound.

In one embodiment, the silicone monomer described here has a formula as set forth in Formulas (I) or (II) below:

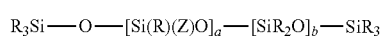

(I)

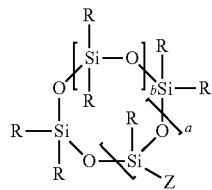

(II)

wherein a is 1 to 50; b is 0 to 100; each R is independently selected from the group comprising of monovalent aliphatic, cycloaliphatic or aromatic hydrocarbon groups of 1 to about 10 carbons, halogenated hydrocarbon groups of 1 to about 10 carbons and radical comprising of 1 to about 50 silicon atoms, or even a trialkylsilyloxy group and Z is a polyether moiety having non-isomerizable hydrosilylation effective terminal olefinic residue having Formula (III):

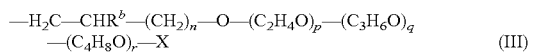

(III)

wherein n is 1 to about 20; p and q are independently 0 to about 100; r is 0 to about 50 and (p+q+r) is greater than 0;

$R^b$ is an alkyl group having from 1 to about 4 carbon atoms, X is a polyether-capping group independently chosen from Formula (IVa) and (IVb):

(IVa)

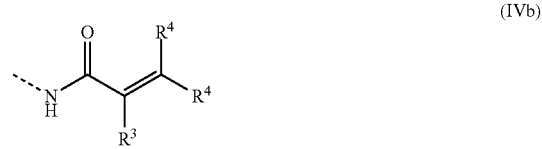

(IVb)

wherein $R^3$ and $R^4$ independently are either hydrogen or a substituted or unsubstituted saturated monovalent hydrocarbon group of 1 to about 20 carbons or —COOH or —CH$_2$—COOH. X can also be vinyl group, or a N-vinyl derivative, or even a N-vinyl-pyrrolidone derivative. The present invention also provides homo and copolymers derived from the described monomers and silicone hydrogels containing the same.

The composition described in the present invention comprises a monomer produced from a process by reacting a silicone-containing compound having Formula (V):

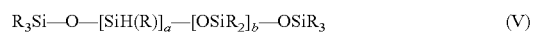

(V)

wherein a is 1 to 50; b is 0 to 100; each R is independently selected from the group consisting of monovalent aliphatic, cycloaliphatic or aromatic hydrocarbon groups of 1 to about 10 carbons and halogenated hydrocarbon groups of 1 to about 10 carbons; with a polyether having at least one end terminated with hydroxyl or halogen or epoxy or amine and the other end terminated with a non-isomerizable hydrosilylation effective terminal olefinic polyether having Formula (VI):

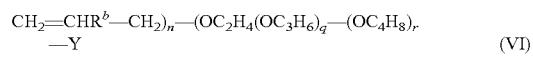

(VI)

wherein n is 1 to about 20; p and q are 0 to about 100; r is 0 to about 50; $R^b$ is an alkyl group having from 1 to about 4 carbon atoms, Y is —OH or a halogen or an epoxy or amine; in the presence of a catalyst to produce a polyether siloxane, and then reacting said polyether siloxane with an acryl compound having Formula (VII):

(VII)

wherein L is a linker group consisting of monovalent aliphatic, cycloaliphatic, or aromatic hydrocarbon radicals of 1 to about 16 carbons optionally containing heteroatoms or halogens.

In another embodiment, L is a moiety having Formula:

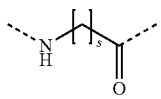

wherein s is an integer selected from 0 to about 15. When L is not utilized, then G is directly linked to the carbonyl group in Formula (VII). G is a halogen or —OH and its organic or inorganic salts, and $R^3$ and $R^4$ independently are either hydrogen or a hydrocarbon group of 1 to about 10 carbons to produce said silicone monomer, or —COOH, or —CH$_2$—COOH.

While not wishing to be bound to any set of advantages, the present invention addresses two major issues simultaneously with silicone-hydrogels of the prior art. It permits incorporation of more hydrophilic units in a polymer molecule thereby leading to more comfortable contact lens composition with retention or improvements in oxygen permeability, Young's modulus and water absorption. Additionally, any post processing steps need less or no organic solvents to clean the lenses and remove any unreacted monomers present.

In another embodiment, the compounds of the present invention are advantageous in that the silicone (meth)acrylamides of present invention do not require additional formulation compatibilizers and/or solvents to yield optically transparent hydrogel lenses.

DESCRIPTION OF THE INVENTION

In accordance with the present invention, new mono-(meth)acrylate functionalized hydrophilic silicone monomer compositions having a polyether moiety containing a branched linking group and useful for preparing water-absorbing silicone-hydrogel films for contact lens applications are described. Silicone hydrogel films obtained with these monomers show better surface wettability, oxygen permeability and desirable modulus in comparison to previously disclosed films made from the corresponding silicone polyether monomers having linear alkyl linking groups. The novel monomers disclosed have a branched linking group in the polyether moiety, which makes it possible to produce hydrophilic polyether modified silicone copolymers without the need to separate unreacted, isomerized polyether and associated high molecular weight by-products.

The present invention relates to compositions comprising a (meth)acrylamide functionalized hydrophilic silicone monomer having a polyether moiety containing a branched linking group. In one embodiment, such compositions are useful for preparing water-absorbing silicone-hydrogel films for contact lens applications. In one embodiment, the (meth)acrylamide monomers disclosed here have a branched linking group on the polyether moiety which makes it possible to produce hydrophilic polyether modified silicone copolymers without the need to separate various by-products including, but not limited to, unreacted, isomerized polyether and associated high molecular weight by-products.

In one embodiment, the present invention relates to hydrogel compositions, and methods of making same. In one embodiment, the present invention comprises a silicone composition containing (meth)acrylamide polyethyleneoxide copolymer formed from the reaction product of free-radical polymerizable siloxane monomers such as TRIS, free-radical polymerizable organic monomers, at least one initiator and, optionally, at least one cross-linking compound. The present invention also comprises hydrogel films from a silicone containing (meth)acrylamide polyethylene oxide homopolymer.

In one embodiment, the silicone monomer described here has a formula as set forth in Formulas (I) or (II) below:

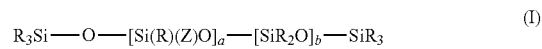

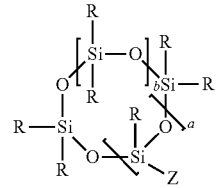

wherein a is 1 to 50; b is 0 to 100; each R is independently selected from the group comprising of monovalent aliphatic, cycloaliphatic or aromatic hydrocarbon groups of 1 to about 10 carbons, halogenated hydrocarbon groups of 1 to about 10 carbons, and radical comprising of 1 to about 50 silicon atoms, or even a trialkylsilyloxy group and Z is a polyether moiety having a non-isomerizable hydrosilylation effective terminal olefinic residue having Formula (III):

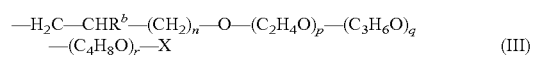

wherein n is 1 to about 20; p and q are independently 0 to about 100; r is 0 to about 50 and (p+q+r) is greater than 0; $R^b$ is an alkyl group having from 1 to about 4 carbon atoms, X is a polyether-capping group independently chosen from Formula (IVa) and (IVb):

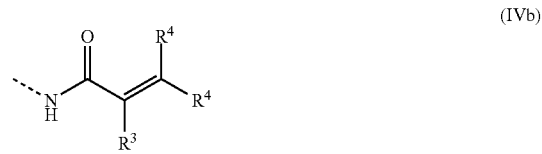

wherein $R^3$ and $R^4$ independently are either hydrogen or a substituted or unsubstituted saturated monovalent hydrocarbon group of 1 to about 20 carbons or —COOH or —CH$_2$—COOH. X can also be vinyl group, or an N-vinyl derivative, or even an N-vinyl-pyrrolidone derivative. The present invention also provides homo and copolymers derived from the described monomers and silicone hydrogels containing the same.

The present invention also comprises a process for producing the described monomers by reacting a silicone-containing compound having Formula (V):

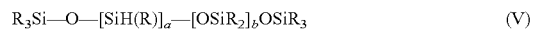

wherein a is 1 to 50; b is 0 to 100; each R is independently selected from the group consisting of monovalent aliphatic, cycloaliphatic or aromatic hydrocarbon groups of 1 to about 10 carbons and halogenated hydrocarbon groups of 1 to about 10 carbons; with a polyether having at least one end terminated with hydroxyl or halogen or epoxy and the other end terminated with a branched alkene having Formula (VI):

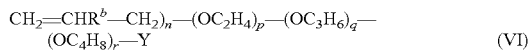

wherein n is 1 to about 20, p and q are 0 to about 100; r is 0 to about 50; $R^b$ is an alkyl group having from 1 to about 4 carbon atoms, Y is —OH or a halogen or an epoxy or amine; in the presence of a catalyst to produce a polyether siloxane, and then reacting said polyether siloxane with an acryl compound having Formula (VII):

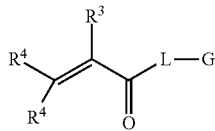

wherein L is a linker group consisting of monovalent aliphatic, cycloaliphatic or aromatic hydrocarbon radicals of 1 to about 16 carbons optionally contains heteroatoms or halogens. In another embodiment, L is a moiety having Formula:

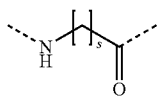

wherein s is an integer selected from 0 to about 15. When L is not utilized, then G is directly linked to the carbonyl group in Formula (VII). G is a halogen or —OH and its organic or inorganic salts, and $R^3$ and $R^4$ independently are either hydrogen or a hydrocarbon group of 1 to about 10 carbons or —COOH or —CH$_2$—COOH to produce said silicone monomer.

While not wishing to be bound to any set of advantages, the present invention addresses two major issues simultaneously with silicone-hydrogels of the prior art. It permits incorporation of more hydrophilic units in a polymer molecule thereby leading to more comfortable contact lens composition with retention or improvements in oxygen permeability, Young's modulus and water absorption. Additionally, any post processing steps need less organic solvents to clean the lenses and remove any unreacted monomers present.

In another embodiment, the compounds of the present invention are advantageous in that the silicone (meth)acrylamide compositions of present invention do not require additional formulation compatibilizers and/or solvents to yield optically transparent hydrogel lenses.

With regard to the above mentioned published PCT patent application, WO 2010/038242, this published application is incorporated by reference in its entirety as if set forth completely herein.

Thus, in light of the above, in one embodiment the present invention, relates to mono-(meth)acrylamide functionalized hydrophilic silicone monomers having a polyether moiety containing a branched linking group. In one instance, the compositions of the present invention are useful for preparing water-absorbing silicone-hydrogel films for contact lens applications. Without being bound to any specific set of advantages, silicone hydrogel films obtained in accordance with the present invention show improved surface wettability, water content and desirable modulus in comparison to previously disclosed silicone polyether methacrylate hydrogel films. In another embodiment, the (meth) acrylamide monomers disclosed herein have a branched linking group on the polyether moiety, which makes it possible to produce hydrophilic polyether modified silicone copolymers without the need to separate unreacted, isomerized polyether and associated high molecular weight by-products.

In one embodiment, the alkyl group, which connects the silicone unit to the hydrophilic polyether chain, is a substituted alkyl group that prevents isomerization of the unsaturated polyether during hydrosilylation step. While not wishing to be bound to any one theory, it is believed that the presence of branched linking group allows greater purity of the silicone-polyether copolymer taken directly from the reactor. In addition, silicone-hydrogel films produced using the present silicone-polyether amide copolymers with branched linking groups show improved water content, and moduli that facilitate lens removal and insertion and that contributes mainly to comfort when lenses are worn.

The monomers of the present invention are also miscible with hydrophilic organic co-monomers as well as hydrophobic silicone monomers (e.g., TRIS) without the aid of any homogenizing agent or solvent, thereby affording silicone compartments that are distributed well across the entire range of monomer—co-monomer compositions to produce uniform silicone hydrogel films.

Suitability of optimal miscibility (optimal solubility parameter) of the described silicone monomer with other organic monomers comes from either or both the chain length of a polyether (hydrophile) or the ratio of alkylene oxides (for example ethylene oxide and propylene oxide) in the polyether chain. If the polyether chain is too short or too long, of the wrong average polarity, or absent, then miscibility with common unsaturated organic monomers can be poor and lead to opaque or translucent materials. Miscibility of silicone-polyether copolymers with unsaturated silicone reactants, solvents and polymers useful for the production of contact lens polymers is also similarly influenced. The size and structure of the silicone group can also be independently varied to influence miscibility, if the amount of silicone relative to polar functional groups is too large, then the organosilicone monomer will be immiscible with polar organic monomers.

In the specific instance that b is zero in Formulas (I) or (II) above, the miscibility with 2-hydroxyethylmethacrylate (HEMA) can be achieved with a Z group of the type: —CH$_2$—CH$_2$—CH$_2$—O—CH$_2$—CH$_2$—OCH$_2$—CH$_2$— OR where at least two ethylene oxide units are present. A reason for this is that the miscibility of these silicone monomers represented by Formula (I) or (II) with polar co-monomers such as 2-hydroxyethylmethacrylate (HEMA) is controlled by the ratio of the silicone moiety to the polar polyether group in the silicone monomer. If no polyether, or too little polyether, is in the silicone monomer, then the silicone monomer is immiscible with HEMA and solvent is required to homogenize them.

Conversely, if too little silicone is present in a silicone-polyether copolymer the desired characteristic of enhanced oxygen transport in a contact lens polymer can be diminished. The materials of the invention can be distributions of compositions resulting from the underlying chemistry of the manufacture of silicone and polyether precursors that are themselves distributions of components. It may be desirable to control the nature of the distribution by chemical and/or physical processes that can remove or reduce the amount of a component or range of components in a distribution that would be less miscible with a particular set of monomers and other constituents in a formulation used to make a contact lens polymer.

Purification of the silicone and/or polyether reactants by distillation, high vacuum stripping, preparative chromatography or supercritical fluid extraction can be used to control the final copolymer distribution. Where small polyether reactants (number average of ether units in the polyether from about two to about six) are to be used to prepare a silicone-polyether copolymer, the removal of the alcohol starter and a single alkylene oxide adduct (that is the starter alcohol reacted with only one alkylene oxide unit) from the distribution is of interest. A purified polyether precursor where unreacted alcohol starter and single alkylene oxide adducts have been removed by distillation or high vacuum stripping, as non-limiting examples, is useful since it could be used as the starter to make short chain (about two to about six) polyether without zero or single ether adducts being present in concentrations that would interfere with a formulation used to produce a contact lens polymer. Treatment of the polyether with ascorbic acid and ascorbates as described in U.S. Pat. No. 5,986,122 improves its hydrosilylation reactivity. Accordingly, U.S. Pat. No. 5,986,122 is incorporated herein in its entirety for its teachings relating to the treatment of a polyether with ascorbic acid and/or ascorbates.

As used herein, "homopolymers" are polymers made from the same repeating monomer and "copolymers" are polymers wherein the polymer contains at least two structurally different monomers. Monomers and polymers with linear alkyl linked (meth)acrylated silicone polyether chains means those compounds without any branching in the linking group that connects the siloxane with the polyalkylene oxide part of the side chain in such compounds. Notations such as (meth)acrylamide denote monomer with either acrylamide or methacrylamide functionality. The monomers of the present invention can be used to obtain cured elastomers with desirable physical strength and resistance to tearing after absorption of water. The mono-(meth)acrylamide functionalized silicone monomers/polymers of the present invention and their preparation and use in contact lens are further described in the sections below.

The present invention also provides silicone-hydrogel compositions comprising (meth)acrylamide functionalized hydrophilic silicone monomer and conventional monomer such as HEMA or other contact lens monomers to produce soft, flexible water absorbing hydrogel films. The homo and copolymers of the present invention are clear (no or less than 1 to 2 percent haze aroused from poor miscibility of monomers) polymers that absorb about 10 weight percent to about 60 weight percent of water, showing excellent surface wettability and sufficient oxygen permeability, all of which are important for comfort when lens are worn and for good health of the human cornea. The present invention also provides contact lenses made from the silicone-hydrogel films of the claimed invention. These embodiments are further described below.

The monomers with high molecular weight polyether chains can be produced in the current invention to form hydrophilic silicone homo/copolymers that can bring silicone-hydrogel films having similar oxygen permeability and significantly improved surface wettability in comparison to monomers like TRIS or linear alkyl linking groups used in the polyether chains. The contact lenses produced from the silicone-hydrogel films of the present invention do not require any expensive secondary treatments, like plasma oxidation or plasma coating, or internal wetting agents to improve wettability. That is, the contact lenses produced from silicone-hydrogel films of the present invention, without secondary treatment, are soft, flexible and inherently wettable and exhibit oxygen permeability.

The monomers of the present invention can be pendant (comb-like) or cyclic with the Formula (I) for pendant structures:

which can be depicted structurally as:

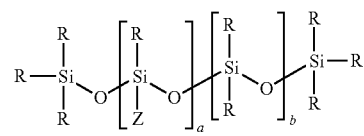

and with the Formula (II) for the cyclic structures being:

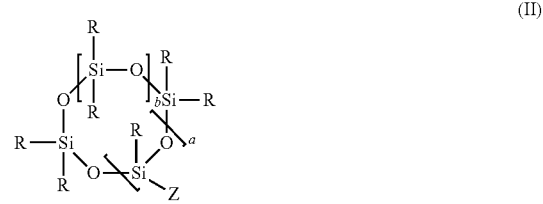

wherein, for both structures, a is 1 to about 50; b is 0 to about 100; each R is independently selected from monovalent aliphatic, or cycloaliphatic hydrocarbon groups of 1 to about 10 carbons, or even 1 to about 6 carbons, or an aromatic hydrocarbon groups of from 1 to about 10 carbons, or even phenyl, or a halogenated hydrocarbon group of 1 to about 10 carbons, or even a fluoro-hydrocarbon or radical comprising of 1 to about 50 silicon atoms, or even a trialkylsilyloxy group.

In the general formulas for the monomer cited above, Z is a polyether with a non-isomerizable hydrosilylation effective terminal olefinic residue having Formula (III):

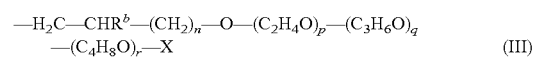

which can be depicted structurally as:

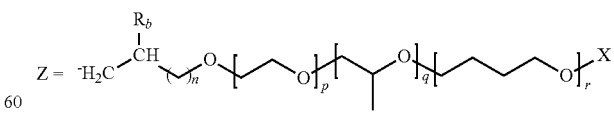

wherein n is 1 to about 20; p and q are 0 to about 100; r is 0 to about 50 and (p+q+r) is greater than 0; and $R^b$ is an alkyl group of from 1 to about 4 carbon atoms, or even a methyl group (—CH$_3$), X is a polyether-capping group independently chosen from the general Formula (IVa) or (IVb):

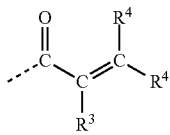

(IVa)

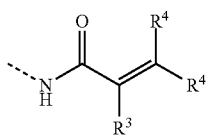

(IVb)

wherein $R^3$ and $R^4$ independently are either hydrogen or a substituted or unsubstituted saturated monovalent hydrocarbon group of 1 to about 20 carbons or —COOH or —CH$_2$—COOH. In the specific instance that b is zero in the monomer formulas above, then the total number of carbon atoms in the polyether group Z is about 6 or greater.

As noted above, the inventive monomers of the present invention can be cyclic. For cyclic monomers of the present invention, the terminal silicon atoms are linked together by an oxygen atom with total (a+b) value is between 3 to about 20. X can also be vinyl group, or an N-vinyl derivative, or even an N-vinyl-pyrrolidone derivative.

The present invention is also directed to polymers formed by the reaction products of the present inventive monomers. These polymers can be homopolymers of one of the monomers of the present invention or copolymers of two structurally different silicone monomers of the present invention and/or copolymers of one or more silicone monomers of the present invention and at least one other hydrophilic unsaturated organic monomer suitable for use in silicone hydrogels, with non-limiting examples of such being N,N-dimethylacrylamide, 2-hydroxy-ethyl-methacrylate (HEMA), N-vinylpyrrolidone, and methacrylic acid. In such copolymers, the copolymer ratio of the silicone monomer of the present invention to the other hydrophilic unsaturated organic monomers is from 1:100 to about 100:1.

To make polymers using the monomer compositions of the present invention, the desired monomers are mixed and the resulting mixture is polymerized and cured to form transparent thin films by known thermal or UV cure techniques, using either peroxides or photoinitiators in the presence of cross-linking agents. The monomers added to the monomer mix to create the mixture prior to polymerization to form the polymers can be monomers or pre-polymers. A "pre-polymer" is a reaction intermediate polymer of medium molecular weight having polymerizable groups. Thus it is understood that the terms "silicone-containing monomers" and "hydrophilic monomers" include pre-polymers. The present invention is also directed to silicone hydrogel films comprising the homopolymers or copolymers detailed above.

One silicone monomer of the present invention has the following Formula:

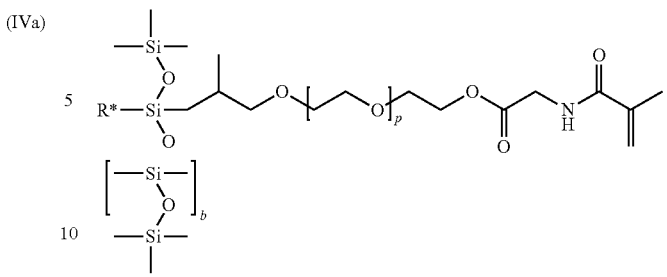

wherein R* is a trialkylsilyloxy group or a methyl group, p is 1 to about 50, or from 2 to about 15, or even about 8, and b is 0 to about 100, or from 0 to 2 inclusive, or even 0. $R^b$ and each of the R groups in the general monomer structure are methyl groups in this monomer.

The other monomers of the present invention have the following structures:

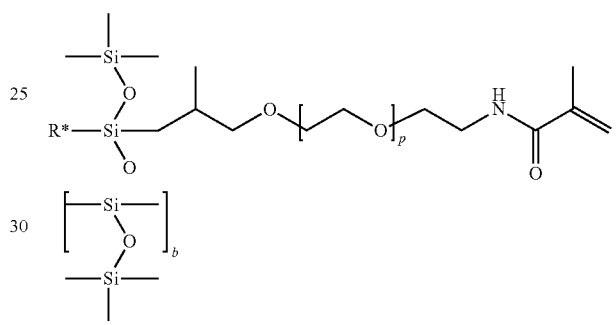

or

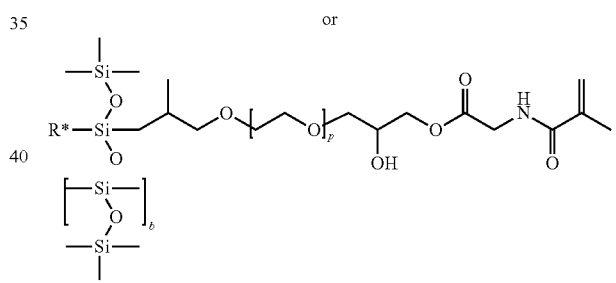

or

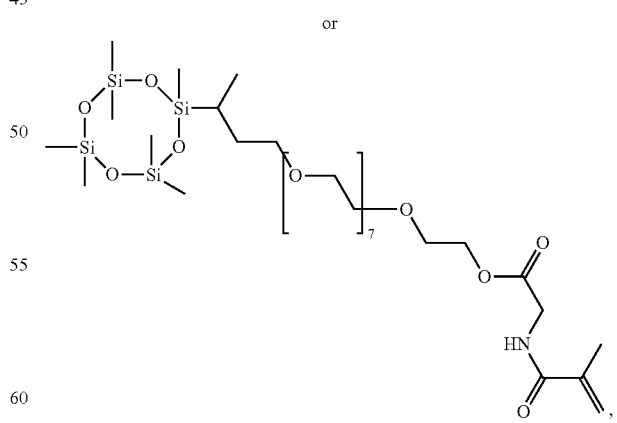

wherein R* is a trialkylsilyloxy group or a methyl group, p is 1 to about 50, or from 2 to about 15, or even about 8, and b is 0 to about 100, or from 0 to 2 inclusive, or even 0. $R^b$ and each of the R groups in the general monomer structure are methyl groups in this monomer.

In another embodiment, the composition described in the present invention comprising a monomer produced from a process by reacting a silicone-containing compound having Formula (V):

$$R_3Si-O-[SiH(R)]_a[OSiR_2]_b-OSiR_3 \quad (V)$$

wherein a, b, and R are defined above; with at least one hydroxyl, halogen or epoxy capped, alkyl branched unsaturated polyether having Formula (VI):

$$CH_2=CHR^b-(CH_2)_n-(OC_2H_4)_p(OC_3H_6)_q(OC_4H_8)_r-Y \quad (VI)$$

which can be depicted structurally as:

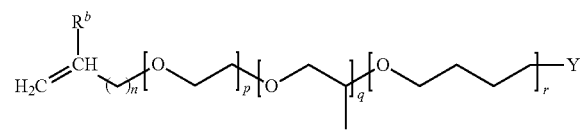

wherein n is 1 to about 20, or from 2 to about 16, or even from 2 to about 6; p and q are individually 0 to about 100; r is 0 to about 50; $R^b$ is an alkyl group attached to the beta carbon of a terminal alkene group, Y is —OH, a halogen or an epoxy or amine; in the presence of a catalyst to produce a polyether siloxane, and then reacting said polyether siloxane with an acryl compound having Formula (VII):

wherein L is a linker group consisting of monovalent aliphatic, cycloaliphatic or aromatic hydrocarbon radicals of 1 to about 16 carbons optionally contains heteroatoms or halogens.

In one embodiment, L has the following formula:

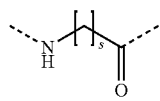

wherein s as an integer varying from 1 to about 5. When L is not used then G is directly linked to the carbonyl group in (VII). G is a halogen or —OH and its organic or inorganic salts, and $R^3$ and $R^4$ independently are either hydrogen or a hydrocarbon group of 1 to about 10 carbons to produce said silicone monomer or —COOH or —CH$_2$—COOH. $R^3$ is, in one embodiment, a methyl group and $R^4$ is, in one embodiment, hydrogen. The reaction of the polyether siloxane with alkylamidoacryloyl compound having Formula (VII) can be carried out in the presence of a tertiary amine base or basic ion-exchange resin (IER) and a low boiling point solvent. Trialkyl amines, such as triethylamine, tripropylamine, and 1 8-diazabicyclo[5.4.0]undec-7-ene (DBU), are suitable bases. The solvent used can be selected from hexane, toluene, tetrahydrofuran, methylethylketone, acetone, dichloromethane, chloroform or other low boiling point solvents with similar polarity (solubility parameter) and inertness under the reaction conditions.

Another embodiment of the present invention is directed to the above-described process wherein, for the formulas above, R and $R^b$ are methyl groups, b is 0; q and r are 0; p is 0 to about 100; or from 0 to about 50; or even from 0 to about 10; Y is OH; and G is chlorine or OH and its organic salt (e.g., DBU salt).

The hydrosilylation reaction of compounds of Formula (V) with those of Formula (VI) can be carried out with or without solvents and additives as described in U.S. Pat. No. 3,229,112; 4,847,398; 4,857,583; 5,191,103; or 5,159,096, the relevant portions thereof being incorporated herein by reference. A major advantage attendant to the selection of the alkyl branched, unsaturated polyether (Formula (VI)) is the use of substantially stoichiometric amounts of the SiH and alkenyl functionalities. Thus, instead of the conventional 10 to 20 percent molar excess of the alkenyl polyether, the hydrosilylation step in synthesis of the instant invention can be done with essentially no molar excess of alkyl branched, unsaturated polyether. SiH/alkenyl stoichiometry in the range 0.99 to 1.09 is effective. Treatment of the polyether with ascorbic acid and ascorbates as taught in U.S. Pat. No. 5,986,122 improves hydrosilylation reactivity and permits use of reduced Pt-catalyst levels. The relevant teachings of this patent have been incorporated herein by reference.

The polymers of the present invention form a clear, transparent homogeneous single-phase solution that can be cured directly without employing any additional homogenizing solvents, depending on the molecular weight of the present siloxane monomers, which are miscible with hydrophilic hydrogel monomers. Calculated solubility parameter values based on Fedors method (See Robert F. Fedors, *Polymer Engineering and Science*, February 1974, vol. 14, No. 2) for the present inventive monomers range from approximately 15 to about 20 $(J/mol)^{2/2}$, this value is close to the solubility parameter of conventional hydrogel monomers (such as HEMA, NVP and DMA) than silicone monomers such as TRIS. Miscibility is realized if the difference in solubility parameter between the instant inventive monomers and the hydrophilic co-monomers is less than about 7.7 $(J/mol)^{1/2}$.

In another embodiment of the present invention, the polymers can be formed into silicone-hydrogel films, via processes known in the art. The silicone-hydrogel films of the present invention are soft, flexible and highly transparent. Silicone-hydrogel films made from the inventive monomers exhibit better surface wettability and sufficiently oxygen permeable compared to ones made using monomers having linear alkyl linked methacrylated silicone polyether chains. The present silicone hydrogel films were found to have dynamic advancing contact angles with water, in the range of 100° to about 20° and absorb about 10 to 70 weight percent of water, which can vary depending on the molecular weight of the polyethers or siloxanes. The contact angle can also be altered in the defined range by adding wetting agents like poly(vinyl pyrrolidone), poly(vinyl alcohol), and hydroxyalkyl cellulose etc. The silicone hydrogels produced were also found to have good mechanical properties (such as low modulus and high tear strength) required for the contact lens application.

Conventional silicone-hydrogel films are generally produced by curing a mixture of hydrophobic silicone monomers and hydrophilic hydrogel monomers in the presence of about 10 to 40 weight percent of solvent or compatibilizer, as they are incompatible with each other. However in the current invention, the inventive silicone methacrylamide monomers are found to be miscible with conventional hydrophilic hydrogel monomers (such as HEMA, NVP and DMA) and can form a homogeneous solution suitable to produce silicone-hydrogel films without employing any solvent or compatibilizer. The densities of the present monomers generally range from 0.89 to 1.1 g/cm$^3$ at 25° C. and the refractive index range from 1.4 to 1.46 for the sodium D line.

The instant inventors have found that monomers with refractive index greater than 1.431 and density greater than 0.96 g/cm$^3$ produce completely miscible compositions or pseudo miscible compositions that appear homogeneous, clear and transparent with hydrophilic monomers like HEMA, in the absence of compatibilizing solvents. As has been stated above, conventional silicone monomers (for example, TRIS) must be mixed with hydrophilic monomers like HEMA in the presence of a solvent to get miscible compositions to make silicone hydrogels. The hydrogel co-monomer used to make silicone-hydrogel copolymers of the present invention can be hydrophilic acrylic monomers such as HEMA, N,N-Dimethyl acrylamide (DMA), N-Vinyl pyrrolidone (NVP), Methacrylic acid (MAA) etc., and optionally, hydrophobic TRIS and polysiloxane analogues.

In the present invention, the resulting polymers can be formed into silicone-hydrogel films, via processes known in the art. Accordingly, the present invention is also directed to a contact lens produced from either homo or copolymers of the present invention. The monomers/polymers of the present invention can be formed into contact lenses by spin-casting processes, as disclosed in U.S. Pat. Nos. 3,408,429 and 3,496,254, cast molding processes, as disclosed in U.S. Pat. Nos. 4,084,459 and 4,197,266, combinations of methods thereof, or any other known method for making contact lenses. It should be noted that the above United States Patents are hereby incorporated by reference for their teachings relating to contact lens production methods. Polymerization can be conducted either in a spinning mold, or a stationary mold corresponding to a desired contact lens shape. The lens may be further subjected to mechanical finishing, as occasion demands. Polymerization can also be conducted in an appropriate mold or vessel to form buttons, plates or rods, which can then be processed (e.g., cut or polished via. lathe or laser) to give a contact lens having a desired shape.

The relative softness or hardness of the contact lenses fabricated from the resulting polymer of this invention can be varied by decreasing or increasing the molecular weight of the polysiloxane pre-polymer end-capped with the activated unsaturated group (such as meth(acryloxy) or (meth) acrylamido) or by varying the percent of the co-monomer. Generally, as the ratio of polysiloxane units to end-cap units increases, the softness of the material increases.

The polymers of this invention can also contain ultraviolet absorbents, pigments and colorants in the form of additives or co-monomers.

As stated above, the silicone-hydrogels of the present invention exhibit sufficient oxygen transport (30 to about 250 Dk) with improved surface wettable properties when compared to silicone-polyether copolymers having linear alkyl linking groups. The oxygen permeability of the hydrogel films can be further extended up to 270 Dk units when silicone monomers described in the current invention are used along with siloxane and polysiloxane analogues known in the art. The monomers and pre-polymers employed in accordance with this invention are readily polymerized to form three-dimensional networks, which permit the transport of oxygen in addition to having improved wettability along with better mechanicals and optical clarity.

For example, the silicone hydrogel film produced with 40 weight percent of the monomer of current invention, along with 10 weight percent of TRIS, 25 weight percent of HEMA, 20 weight percent of DMA and 5 weight percent of NVP co-monomers exhibits a Young's modulus value of 0.8 MPa with greater than 95 percent optical transmission and captive bubble contact angle below 30° proving that the silicone monomers described in the current invention is suitable for making contact lens formulations along with both commercial hydrophobic and hydrophilic siloxane or organic co-monomers. It is noticed that when the silicone monomer used is Example 1 (40 weight percent), along with 10 weight percent of TRIS, 25 weight percent of HEMA, 20 weight percent of DMA and 5 weight percent of NVP in the presence of a UV initiator 1 percent by weight of the formulation started curing at 365 nm within 10 seconds and produced self-standing film within 25 to 30 seconds. The curing is more than 90 percent complete by 25 to 50 seconds. The overall methyl hydroquinone inhibitor content of the total formulation is around 100 PPM. The formulations made with methacrylamides of the current invention have excellent curing properties compared to example-6 known in the art.

Specific use of the hydrogel films include intraocular contact lenses, artificial corneas, and soft disposable long-wear contact lenses or as coatings for biomedical devices.

In one aspect, the hydrophilic silicone monomer can be used in preparation of homo or copolymers with other free radical polymerization effective monomers to form materials in bulk or latex form. These homopolymer, copolymer, emulsion and latex particles comprising the monomer of current invention can be used as ingredients in personal care formulations including skin care, hair care, and nail care, such as lipsticks, mascaras, foundations, lotions, creams, shampoos, conditioners and nail polishes, to improve their ware, tactile properties and ease of application. They also can be used in textile and fiber treatment applications to impart smooth, soft feel and wettability to both natural and synthetic fibers. Finally the homopolymer, copolymer, emulsion and latex particles can be incorporated into coating formulations for metal, plastic, wood and paper, such as varnishes, latex paints and roofing compositions.

EXAMPLES

Specific Examples from 1, 2, 3, 4, 5, and 7 are according to current invention, while Example 6 (Methacrylated trisiloxane polyoxyethylene copolymer with an average of four ethylene oxide units) is a comparative example.

Monomer Preparation

Example 1

Synthesis of the compound represented by the formula

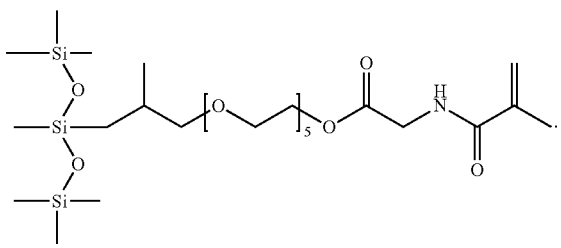

Methacrylamide containing silicone-polyether monomers are prepared using a four-step process. In a first step, a hydrosilylation reaction occurs between hydroxyl terminated methallyl polyether and mono-hydride functional trisiloxane moiety. The terminal hydroxyl group is converted into a good leaving group in the second step through a tosylation reaction. The third step involves the methacrylation of glycine, preparation of a reactant for the last step. In the last step, an SN$^2$ reaction of tosylate using glycine methacrylamide salt produced the desired target.

In this instance, heptamethyl-trisiloxane (70 grams) and a methallyl-terminated polyethylene glycol (75 grams), having an average of four ethylene oxide (EO) units in the chain, are introduced into a 500 mL three-neck round bottom flask equipped with a reflux condenser, mechanical stirrer, temperature controller with thermocouple and a nitrogen inlet. The contents are heated to 80° C. to 85° C. in the presence of Karstedt's catalyst (platinum complex of 1,3-divinyltetramethyldisiloxane, 30 ppm Pt based on weight of total reactants charged) and 50 ppm sodium propionate buffer (see U.S. Pat. No. 4,847,398). After completion of the hydrosilylation, volatile compounds (for example, toluene introduced with the catalyst) are distilled (stripped) under reduced pressure. The final product, hydroxyl terminated silicone polyether, is obtained as a colorless, transparent liquid in quantitative yield without any undesired side products. The resultant pure product is well characterized by multinuclear NMR ($^1$H, $^{13}$C, $^{29}$Si) spectroscopy and gel permeation chromatography (GPC). Synthesis of the silicone polyethers of the present invention can occur with or without a solvent. If one or more solvents are used, suitable ones include toluene, isopropyl alcohol or methyl ethyl ketone.

Tosylation is carried out by placing the hydroxyl terminated silicone polyether (100 grams, 0.2 moles) and triethylamine (82 mL, 0.59 moles) in a 500 mL three-neck round bottom flask fitted with a reflux condenser and a dropping funnel. The nitrogen gas is continuously purged during the reaction at rate of about 20 to 30 bubbles per second in a bubbler connected to the third neck of the flask using an adapter and a rubber tube. To a stirring reactant is added anhydrous tetrahydrofuran (200 mL) and continued stirring. The reaction temperature is increased to 35° C. and maintained throughout the reaction. p-toluenesulfonyl chloride (48.2 grams, 0.25 moles) solution in anhydrous tetrahydrofuran is added drop wise for 40 to 45 minutes. A white precipitate of triethylammonium hydrochloride salt comes out within 45 minutes of the reaction. The reaction time is 4 to 5 hours. After the reaction, organic salt is filtered out and the filtrate is concentrated under reduced pressure on a rotary evaporator. After removal of the solvent some more organic salt separates out of the product after storage for 12 hours at 27° C. Filtration resulted in a tosylate terminated silicone polyether in quantitative yield. This product is confirmed by the NMR technique.

Twenty-five grams (0.33 mol) of glycine is added pinch by pinch to 250 mL round bottom flask containing aqueous NaOH solution (34 grams, 0.83 moles) in 100 mL deionized water. The flask is cooled to 0 to 5° C. using ice-salt bath. Methacryloyl chloride (39 mL, 0.39 moles) is added drop wise for 30 to 45 minutes maintaining the bath temperature below 5° C. Then the reaction mixture is allowed to warm to room temperature. The reaction mixture is acidified to pH 3 and extracted 4 times with ethyl acetate (40 mL×4). The ethyl acetate layer is separated using a separating funnel and transferred to a conical flask containing anhydrous sodium sulfate (50 grams). The ethyl acetate is decanted to round bottom flask and the solvent is removed under reduced pressure to obtain glycine methacrylamide as a white solid powder (>70% yield). This product is confirmed by the NMR technique.

For SN$^2$ reaction, the tosylate terminated silicone polyether (25 grams, 0.04 moles) is reacted with 1,8-Diazabicyclo[5.4.0]undec-7-ene (DBU) (6.26 grams, 0.041 moles) and glycine methacrylamide (5.31 grams, 0.041 moles) using N,N-dimethylformamide (30 mL) as the solvent in a 250 mL two-neck round bottom flask fitted with a reflux condenser, heating bath and a nitrogen bubbler. One hundred to two hundred ppm of hydroquinone is used during the reaction to avoid unexpected polymerization. The temperature of the heating bath is maintained at 65° C. during the reaction. After 12 hours, N,N-dimethylformamide is removed under reduced pressure using a rotary evaporator (70° C., 20 mbar). The crude material is dissolved in 25 mL chloroform and washed with brine solution (15 mL×3). The chloroform layer is separated, dried over anhydrous Na$_2$SO$_4$, decolorized from activated charcoal, and the solvent is removed under reduced pressure in a rotary evaporator. The final product is obtained in quantitative yield.

The final product is well characterized by infrared spectroscopy, multinuclear NMR ($^1$H, $^{13}$C, $^{29}$Si) spectroscopy. The proton and silicon NMR results of the final monomer are: $^1$H-NMR, 300 MHz, CDCL$_3$ (ppm): 0.03 to 0.17 (br. m, 21H, CH$_3$Si—), 0.21 to 0.35 (m, 1H, Si—CH$_2$), 0.52 to 0.64 (m, 1H, Si—CH$_2$—), 0.95 (d, J=9 Hz, 3H, —CH$_3$), 1.82 to 1.95 (m, 1H, —CH(R)), 1.99 (br. S, 3H, =C(CH$_3$)), 3.07 to 3.2 (m, 1H, R—CH$_2$CH$_2$O—), 3.22 to 3.35 (m, 1H, R—CH$_2$CH$_2$O—), 3.40 to 3.97 (m, 18H, —(CH$_2$CH$_2$O)$_n$—), 4.08 to 4.18 (m, 2H, NH—CH$_2$COO—), 4.27 to 4.40 (m, 2H, OOC—CH$_2$) 5.38 (br. S, 1H, =CH$_2$), 5.77 (br. S, 1H, =CH$_2$), 6.45 (br. S, 1H, —NH—CO). $^{29}$Si-NMR, 79.51 MHz, CDCL$_3$ (ppm): −21.9 (—OSi—(CH$_3$)(EO)), 7.2 (—OSi(CH$_3$)$_3$).

Example 2

Synthesis of the compound represented by the following formula:

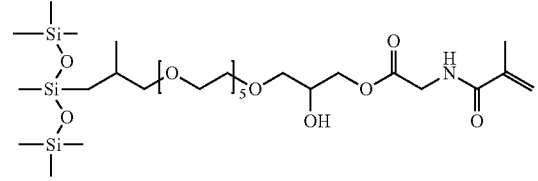

An epoxy terminated polyether with average molecular structure of CH$_2$CH(CH$_3$)O(CH$_2$CH$_2$O)$_5$CH$_2$CHOCH$_2$ is synthesized by reacting a hydroxyl terminated polyether of average structure CH$_2$CH(CH$_3$)O(CH$_2$CH$_2$O)$_5$H (MAPEG5) with epichlorohydrin as follows: 50 grams of MAPEG5, 50 mL hexane and 0.4 grams of cetyltrimethylammonium bromide (CTAB) are placed in a 250 mL round bottom flask fitted with a condenser and a dropping funnel. To this is charged 10.2 grams of solid NaOH, the resulting material is mixed with the help of a magnetic stirrer and slowly heated to 40° C. to 42° C. To this mixture is added 31.6 grams of epichlorohydrin drop wise over two hours. The reaction is continued for another 4 hours. After this the salts and excess base are removed by filtering and the filtrate is subjected to vacuum stripping at 15 mbar while slowly raising the temperatures to 85° C. This yields a viscous, clear epoxy capped polyether with 95 percent epoxy capping—as confirmed by $^1$H-NMR and is used for the next step.

In the hydrosilylation step, heptamethyl-trisiloxane (50 grams, 0.23 moles) and a polyethylene glycol (78.5 grams, 0.23 moles) terminated with a methallyl group on one side and an epoxy group on the other side, having an average of five ethylene oxide (EO) units in the chain, are introduced into a 250 mL three-neck round bottom flask equipped with a reflux condenser, mechanical stirrer, temperature controller with thermocouple and a nitrogen inlet. The contents are heated to 80° C. to 85° C. in the presence of Karstedt's catalyst (platinum complex of 1,3-divinyltetramethyldisiloxane, 30 ppm Pt based on weight of total reactants charged) and 100 ppm sodium propionate buffer (see U.S. Pat. No. 4,847,398). After completion of the hydrosilylation, volatile compounds (for example, toluene introduced with the catalyst) are distilled (stripped) under reduced pressure. The final product, epoxy terminated silicone polyether, is obtained as a colorless, transparent liquid in quantitative yield without any undesired side products. The resultant pure product is well characterized by multinuclear NMR ($^1$H, $^{13}$C, $^{29}$Si) spectroscopy and gel permeation chromatography (GPC). Synthesis of the silicone polyethers of the present invention can occur with or without solvent. If solvents are used, suitable ones include toluene, isopropyl alcohol or methyl ethyl ketone.

In the last step, epoxy terminated silicone polyether (25 grams, 0.044 moles) is mixed with methyl ethyl ketone solvent (50 mL) and 2,2,6,6-tetramethyl-piperidinooxy free radical (TEMPO) (0.004 g, $2.2 \times 10^{-5}$ mol) as the polymerization inhibitor. At 70° C., titanium isopropoxide (0.5 weight percent) is added followed by the addition of glycine methcrylate. The reaction is continued for 24 hours at 90° C. After 24 hours, the titanium oxides formed is removed by filtration over celite bed (2 cm) taken in a Buckner funnel. The celite is washed with methyl ethyl ketone (10 mL×2) and the filtrate is concentrated under reduced pressure. The final product is decolorized using activated charcoal. The final product is obtained as pale brown colored oil.

The proton and silicon NMR data of the final monomer are: $^1$H-NMR, 300 MHz, CDCl$_3$ (ppm): 0.01 to 0.14 (br. m, 21H, CH$_3$Si—), 0.21 to 0.32 (m, 1H, Si—CH$_2$—), 0.51 to 0.62 (m, 1H, Si—CH$_2$—), 0.94 (d, J=9 Hz, 3H, —CH$_3$), 1.83 to 1.95 (m, 1H, —CH(R)), 1.98 (br. S, 3H, =C(CH$_3$), 3.08-3.16 (m, 1H, R—CH$_2$CH$_2$O—), 3.24 to 3.32 (m, 1H, R—CH$_2$CH$_2$O—), 3.48 to 3.75 (m, 18H, —(CH$_2$CH$_2$O)$_n$—), 4.11 to 4.15 (m, 2H, NH—CH$_2$COO—), 4.22 to 4.26 (m, 2H, OOC—CH$_2$) 5.38 (br. S, 1H, =CH$_2$), 5.77 (br. S, 1H, =CH$_2$), 6.49 (br. S, 1H, —NH—CO). $^{29}$Si-NMR, 79.51 MHz, CDCl$_3$ (ppm): -21.9 (—OSi—(CH$_3$)(EO)), 7.1 (—OSi(CH$_3$)$_3$).

Example 3

Synthesis of the compound represented by the following formula:

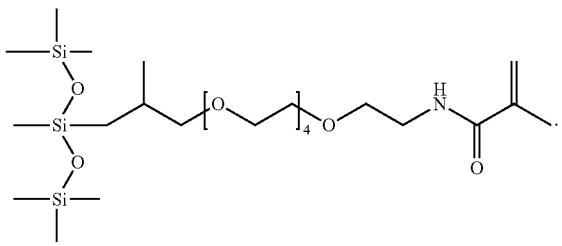

The synthetic route makes use of Gabriel Phthalimide reactions. The tosylate terminated silicone polyether described in Example 1 is reacted with potassium phthalimide, which is hydrazinalised in the next step to produce the amine terminated silicone polyether. The amine terminated silicone polyether is methacrylated in the final step.

The tosylate terminated silicone polyether (25 grams, 0.037 moles) is placed in a 500 mL round bottom flask fitted with a nitrogen flow system. To this flask is added N,N-dimethyl formamide (50 mL) followed by the addition of potassium phthalimide (8.3 grams, 0.045 moles). The resulting mixture is stirred at 65° C. for 12 hours. After 12 hours, the reaction mixture is filtered and the filtrate is concentrated under reduced pressure to obtain semi-solid material. This semi-solid material is stirred in hexane and the resulted comes are filtered again and concentrated under reduced pressure. The final product, a phthalimide terminated silicone polyether, is isolated as light yellow colored viscous oil in quantitative yield.

Phthalimide terminated silicone polyether (20 grams, 0.031 moles) is mixed with ethyl alcohol in a two-neck round bottom flask fitted with a reflux condenser under nitrogen environment. The solution is refluxed at 95° C. Refluxing is continued after adding hydrazine hydrate (1.71 grams, 0.034 moles) 50 percent v/v solution in ethyl alcohol in one shot for 3 hours. A strong white precipitate appears within 5 minutes after addition of hydrazine hydrate. After 3 hours, the reaction mixture is filtered using a Whatmann-1 filter paper. The filtrate is rotary evaporated under reduced pressure to remove ethyl alcohol. The semi-solid product obtained is diluted with hexane and filtered. The filtrate is evaporated under reduced pressure to obtain amine terminated silicone polyether as pale yellow oil in quantitative yield.

Amine terminated silicone polyether (15 grams, 0.027 moles) is dissolved in toluene (25 mL) in a 250 mL two-neck round bottom flask fitted with a dropping funnel under nitrogen environment. Triethylamine (3.2 mL, 0.033 moles) is added to the reaction flask. The round bottom flask is kept in an ice bath and the reaction temperature is maintained below 5° C. Methacryloyl chloride (4.6 grams, 0.033 moles) is added drop wise to the reaction mixture for 15 to 20 minutes. The reaction mixture is allowed to warm up to room temperature and stirring is continued for 3 hours. Then, the reaction mixture is filtered to remove triethylamine hydrochloride as the first by-product. The filtrate is stirred over Thermax 8XMP (Tulsion from Thermax India Ltd.) basic ion exchange resin to remove methacrylic acid as the second by-product. Finally, the material is stirred over activated charcoal to obtain the final methacrylamide terminated silicone polyether as pale yellow oil in quantitative yield.

The proton and silicon NMR data of the final monomer are: $^1$H-NMR, 300 MHz, CDCl$_3$ (ppm): 0.01 to 0.18 (br. m, 21H, CH$_3$Si—), 0.23 to 0.36 (m, 1H, Si—CH$_2$), 0.52 to 0.65 (m, 1H, Si—CH$_2$—), 0.96 (d, J=9 Hz, 3H, —CH$_3$), 1.83 to 1.95 (m, 1H, —CH(R)), 1.97 (br. S, 3H, =C(CH$_3$), 3.09 to 3.19 (m, 1H, R—CH$_2$CH$_2$O—), 3.24 to 3.35 (m, 1H, R—CH$_2$CH$_2$O—), 3.46 to 3.95 (m, 18H, —(CH$_2$CH$_2$O)$_n$—), 5.34 (br. S, 1H, =CH$_2$), 5.72 (br. S, 1H, =CH$_2$), 6.44 (br. S, 1H, —NH—CO). $^{29}$Si-NMR, 79.51 MHz, CDCl$_3$ (ppm): -22 (—OSi—(CH$_3$)(EO)), 7.1 (—OSi(CH$_3$)$_3$).

Example 4

Synthesis of the compound represented by the following formula:

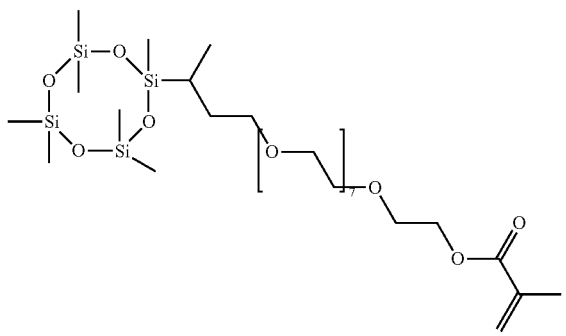

Hexamethylcyclotrisiloxane or D$_3$ (21 grams, 9.44 mmoles) and dichloromethylsilane (12.0 grams, and 10.4 mmoles) are placed in a three-neck 250 mL round bottom flask. The flask is heated to 40° C. for 10 minutes. Heating is stopped and Hexamethylphosphoric triamide (10 µL) is added to the reaction mixture while stirring. The reaction mixture is then stirred for 30 minutes and the progress is monitored by running a $^1$H NMR spectrum. The reaction mixture is then slowly added drop wise (using a dropping funnel) to a stirring solution of diisopropyl ether (50 mL) and water (20 mL) in a three-neck 250 mL round bottom flask for over 60 minutes at room temperature. The stirring is continued for an additional 60 minutes. The organic layer is separated, neutralized with 7 percent NaHCO$_3$ solution (2×50 mL) followed by a water wash (40 mL), dried over anhydrous sodium sulfate and evaporated to yield a crude heptamethylcyclotetrasiloxane (D$_3$D$^H$). This is then purified by vacuum distillation to give 63 percent D$_3$D$^H$ as a colorless liquid (performed at 90° C./20 mm of Hg). The product is then characterized by $^1$H and $^{29}$Si NMR.

D$_3$D$^H$ (14.9 grams, 5.27 mmoles) and methallyl polyoxyethylene (8 EO chains) (22.3 grams, 5.27 mmoles), sodium propionate (100 ppm) are heated to 70° C. in a two-neck round bottom flask equipped with a reflux condenser. Then Karstedt's catalyst (30 ppm as diluted 2-propanol solution) is added to the above mixture and the temperature is raised to 90° C. The stirring is continued for 3 hours. The reaction is monitored by running $^1$H NMRs of the reaction mixture. After completion, the reaction mixture is then cooled to room temperature to yield a dark yellow colored liquid which is then decolorized with activated charcoal (1 gram) to yield a colorless oil of hydroxyl terminated cyclic siloxane polyether copolymer in quantitative yield. The hydrosilylated product is characterized by $^1$H and $^{29}$Si NMR.

The hydroxyl terminated cyclic siloxane polyether copolymer (50 grams, 0.071 moles), triethylamine (16.5 mL, 0.12 moles) and toluene (50 mL) are taken in a two-neck round bottom flask fitted with a dropping funnel and a mechanical stirrer under nitrogen environment. The whole set-up is kept in an ice bath with reaction temperature maintained below 5° C. To a stirring reaction mixture is added methacryloyl chloride (8.3 mL, 0.085 moles) drop wise for a period of 30 minutes. The reaction is allowed to warm to room temperature under continued stirring for about 3 hours. The triethyl ammonium chloride salt is filtered off and the filtrate is mixed with Thermax 8XMP (Tulsion from Thermax India Ltd.) basic ion exchange resin (25 grams) and stirred for 12 hours. The mixture is then filtered and decolorized with activated charcoal (1 gram) and solvent is evaporated under reduced pressure to yield methacrylated cyclic siloxane polyether copolymer in quantitative yield. The final product is characterized by $^1$H and $^{29}$Si NMR.

$^1$H-NMR, 300 MHz, CDCl$_3$ (ppm): 0.08 (br. s, 21H, CH$_3$Si—), 0.26 to 0.40 (m, 1H, Si—CH$_2$), 0.61 to 0.72 (m, 1H, Si—CH$_2$—), 0.96 (d, J=9 Hz, 3H, —CH$_3$), 1.86 to 1.9 (m, 1H, —CH(R)), 1.94 (br. S, 3H, =C(CH$_3$), 3.11 to 3.21 (m, 1H, R—CH$_2$CH$_2$O—), 3.24 to 3.31 (m, 1H, R—CH$_2$CH$_2$O—), 3.52 to 3.89 —(CH$_2$CH$_2$O)$_n$—), 4.27 to 4.34 (m, 2H, CH$_2$CH$_2$COO—), 5.56 (br. S, 1H, =CH$_2$), 6.13 (br. S, 1H, =CH$_2$). $^{29}$Si-NMR, 79.51 MHz, CDCl$_3$ (ppm): -18.9 (—OSi—(CH$_3$)$_2$—O), -19.2 (—OSi—(CH$_3$)$_2$—O), -20.1 (—OSi—(CH$_3$)(EO)—O—).

Example 5

Synthesis of compound represented by the following formula:

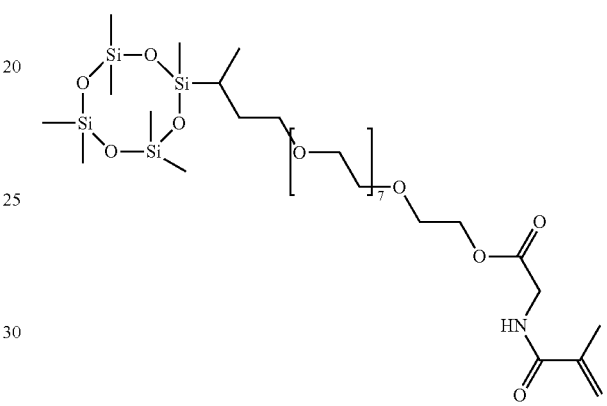

The synthesis is started from D3 and dichloromethyl silane to obtain D$_3$D$^H$ and then hydrosilylated with methallyl polyether containing 8-EO chains as described in Example 4 above.

Tosylation is carried out by placing the hydroxyl terminated cyclic silicone polyether (25 grams, 0.035 moles) and triethylamine (8.3 mL, 0.06 moles) in a 250 mL three-neck round bottom flask fitted with a reflux condenser and a dropping funnel. The nitrogen gas is continuously purged during the reaction at rate of about 20 to 30 bubbles per second in a bubbler connected to the third neck of the flask using an adapter and a rubber tube. To a stirring reactant is added anhydrous tetrahydrofuran (50 mL) and stirring is continued. The reaction temperature is increased to 65° C. and maintained throughout the reaction. p-toluenesulfonyl chloride (8.1 grams, 0.042 moles) solution in anhydrous tetrahydrofuran (20 mL) is added drop wise for 40 to 45 minutes. A white precipitate of triethylammonium hydrochloride salt comes out within 45 minutes of the reaction. The reaction time is 4 to 5 hours. After the reaction, organic salt is filtered out and the filtrate is concentrated under reduced pressure on a rotary evaporator. After removal of the solvent some more organic salt separates out of the product after storage for 12 hours at 27° C. Filtration results in a tosylate terminated silicone polyether in quantitative yield. This product is confirmed by the NMR technique.

The tosylate terminated cyclic silicone polyether (10 grams, 0.012 moles) is reacted with 1,8-Diazabicyclo[5.4.0]undec-7-ene (DBU) (1.94 grams, 0.013 moles) and glycine methacrylamide (1.65 grams, 0.013 moles) using N,N-dimethylformamide (15 mL) as the solvent in a 100 mL two-neck round bottom flask fitted with a reflux condenser, heating bath and a nitrogen bubbler. One hundred to two hundred ppm of hydroquinone is used during the reaction to avoid unexpected polymerization. The temperature of the heating bath is maintained at 65° C. during the reaction. After 12 hours, N,N-dimethylformamide is removed under reduced pressure using a rotary evaporator (70° C., 20 mbar). The crude material is dissolved in 25 mL chloroform and washed with brine solution (15 mL×3). The chloroform layer is separated, dried over anhydrous $Na_2SO_4$, decolorized from activated charcoal, and the solvent is removed under reduced pressure in a rotary evaporator. The final product is obtained in quantitative yield.

The final product is well characterized by infrared spectroscopy, multinuclear NMR ($^1H$, $^{13}C$, $^{29}Si$) spectroscopy. $^1H$-NMR, 300 MHz, $CDCl_3$ (ppm): 0.08 (br. s, 21H, $CH_3Si$—), 0.26 to 0.41 (m, 1H, Si—$CH_2$), 0.61 to 0.73 (m, 1H, Si—$CH_2$—), 0.97 (d, J=9 Hz, 3H, —$CH_3$), 1.89 to 1.96 (m, 1H, —CH(R)), 1.99 (br. S, 3H, =$C(CH_3)$, 3.11 to 3.2 (m, 1H, R—$CH_2CH_2O$—), 3.24 to 3.32 (m, 1H, R—$CH_2CH_2O$—), 3.54 to 3.76 —$(CH_2CH_2O)_n$—), 4.11 to 4.18 (m, 2H, NH—$CH_2COO$—), 4.29 to 4.36 (m, 2H, OOC—$CH_2$) 5.39 (br. S, 1H, =$CH_2$), 5.78 (br. S, 1H, =$CH_2$), 6.45 (br. S, 1H, —NH—CO). $^{29}Si$-NMR, 79.51 MHz, $CDCl_3$ (ppm): —18.8 (—$OSi(CH_3)_2$—O), -19.1 (—$OSi(CH_3)_2$—O), -20.2 (—OSi—$(CH_3)(EO)$—O—).

Example 6

Synthesis of compound represented by the formula

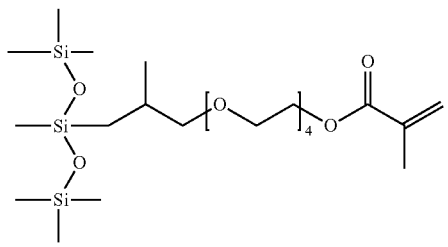

The methacrylated silicone-polyether monomers were prepared using a two-step process. In a first step, a hydrosilylation reaction occurs between hydroxyl terminated methallyl polyether and mono-hydride functional trisiloxane moiety. In the second step, the hydroxyl group is converted into the polymerizable methacrylate group through a methacrylation reaction.

In a specific process, heptamethyl-trisiloxane (70 g) and a methallyl-terminated polyethylene glycol, having an average of four ethylene oxide (EO) units in the chain, (75 g) were introduced into a 500 mL three-neck round bottom (RB) flask equipped with a reflux condenser, mechanical stirrer, temperature controller with thermocouple and a nitrogen inlet. The contents were heated to 80° C.-85° C. in the presence of Karstedt's catalyst (platinum complex of 1,3-divinyltetramethyldisiloxane, 30 ppm Pt based on weight of total reactants charged) and 50 ppm sodium propionate buffer (see U.S. Pat. No. 4,847,398). After completion of the hydrosilylation, volatile compounds (for example, toluene introduced with the catalyst) were distilled (stripped) under reduced pressure. The final product, hydroxyl terminated silicone polyether, was obtained as a colorless, transparent liquid in quantitative yield without any undesired side products. The resultant pure product was well characterized by multinuclear NMR ($^1H$, $^{13}C$, $^{29}Si$) spectroscopy and gel permeation chromatography (GPC). Synthesis of the silicone polyethers of the present invention can occur with or without solvent. If solvents are used, preferred ones include toluene, isopropyl alcohol or methyl ethyl ketone.

Next, the silicone polyether (142 g) that was synthesized in the step above, triethylamine (30.3 g) (or alternatively basic ion-exchange resin acid scavenger), and methyl ethyl ketone (250 ml) were introduced into a three-neck one liter RB flask equipped with dropping funnel and a stirring blade. The flask was immersed in an ice bath and methacryloyl chloride (31.3 g) was added drop wise over a period of approximately 1 hour with constant stirring. After completion of the addition, the stirring was continued for another 3 hours at room temperature. The triethylamine hydrochloride salt thus formed precipitated out during the reaction. When the ion exchange resin was used, it was filtered off. The solvent was removed with a rotary vacuum evaporator and the final monomer was obtained as a colorless, transparent liquid. The low boiling point of the solvent used enabled the solvent to be removed completely at a temperature of about 30° C. to 40° C. under vacuum (i.e. less than about 10 mm Hg). The resulting hydrophilic monomer product was colorless to pale yellow. It was stored in amber bottle in a refrigerator. Characterization by infrared spectroscopy, multinuclear NMR ($^1H$, $^{13}C$, $^{29}Si$) spectroscopy $^1H$-NMR, 300 MHz, $CDCl_3$ (ppm): 0.07 (($CH_3)Si$—), 0.26, 0.56 (Si—$CH_2$—), 0.95 (—$CH_3$), 1.93 (=$C(CH_3)$), 3.64 (—$CH_2CH_2O$—), 4.29 ($CH_2COO$), 5.56, 6.12 (=$CH_2$). $^{29}Si$-NMR, 79.51 MHz, $CDCl_3$ (ppm): -22 (—$OSi(CH_3)$ (EO)), 7 (—$OSi(CH_3)_3$).

Example 7

Specific synthesis of the compound represented by the formula

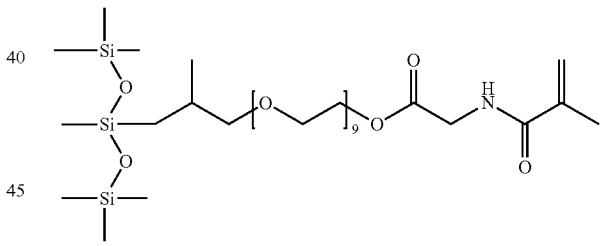

The process involves four-steps. First step, a hydrosilylation reaction occurs between hydroxyl terminated methallyl polyether and mono-hydride functional trisiloxane moiety. The terminal hydroxyl group is converted into a good leaving group in the second step through a tosylation reaction. Third step involves the methacrylation of glycine, preparation of a reactant for the last step. In the last step, $SN^2$ reaction of tosylate using glycine methacrylamide salt produced the desired target.

In this instance, heptamethyl-trisiloxane (100 grams) and a methallyl-terminated polyethylene glycol (209 grams), having an average of nine ethylene oxide (EO) units in the chain, are introduced into a 1000 mL three-neck round bottom flask equipped with a reflux condenser, mechanical stirrer, temperature controller with thermocouple and a nitrogen inlet. The contents are heated to 80° C. to 85° C. in the presence of Karstedt's catalyst (platinum complex of 1,3-divinyltetramethyldisiloxane, 30 ppm Pt based on weight of total reactants charged) and 50-100 ppm sodium propionate buffer (see U.S. Pat. No. 4,847,398). After completion of the hydrosilylation, volatile compounds (for example, toluene introduced with the catalyst) are distilled (stripped) under reduced pressure. The final product, hydroxyl terminated silicone polyether, is obtained as a colorless, transparent liquid in quantitative yield (302 grams, isolated) without any undesired side products. The resultant pure product is well characterized by multinuclear NMR ($^1$H, $^{13}$C, $^{29}$Si) spectroscopy and gel permeation chromatography (GPC). Synthesis of the silicone polyethers of the present invention can occur with or without a solvent. If one or more solvents are used, suitable ones include toluene, isopropyl alcohol or methyl ethyl ketone.

Tosylation is carried out by placing the hydroxyl terminated silicone polyether (100 grams, 0.15 moles) and triethylamine (53 mL, 0.36 moles) in a 500 mL three-neck round bottom flask fitted with a reflux condenser and a dropping funnel. The nitrogen gas is continuously purged during the reaction at rate of about 20 to 30 bubbles per second in a bubbler connected to the third neck of the flask using an adapter and a rubber tube. To a stirring reactant is added anhydrous tetrahydrofuran (50 mL) and continued stirring. The reaction temperature is increased to 35° C. and maintained throughout the reaction. p-toluenesulfonyl chloride (35.9 grams, 0.19 moles) is added pinch by pinch for 40 to 45 minutes. A white precipitate of triethylammonium hydrochloride salt comes out within 45 minutes of the reaction. The reaction time is usually 4 to 5 hours, to ensure completion, normally kept for 24 hours. After the reaction, organic salt is filtered out and the filtrate is concentrated under reduced pressure on a rotary evaporator. After removal of the solvent some more organic salt separates out of the product after storage for about 12 hours at 22-25° C. Filtration resulted in a tosylate terminated silicone polyether in quantitative yield (89 gram, isolated yield). This product is confirmed by the NMR technique.

Twenty-five grams (0.33 mol) of glycine is added pinch by pinch to 250 mL round bottom flask containing aqueous NaOH solution (34 grams, 0.83 moles) in 100 mL deionized water. The flask is cooled to 0 to 5° C. using ice-salt bath. Methacryloyl chloride (39 mL, 0.39 moles) is added drop wise for 30 to 45 minutes maintaining the bath temperature below 5° C. Then the reaction mixture is allowed to warm to room temperature. The reaction mixture is acidified to pH 3 and extracted 4 times with ethyl acetate (40 mL×4). The ethyl acetate layer is separated using a separating funnel and transferred to a conical flask containing anhydrous sodium sulfate (50 grams). The ethyl acetate is decanted to round bottom flask and the solvent is removed under reduced pressure to obtain glycine methacrylamide as a white solid powder (>70% yield). This product is confirmed by the NMR technique.

For the SN$^2$ reaction, the tosylate terminated silicone polyether (25 grams, 0.03 moles) is reacted with 1,8-Diazabicyclo[5.4.0]undec-7-ene (DBU) (5.4 grams, 0.04 moles) and glycine methacrylamide (5.4 grams, 0.04 moles) using N,N-dimethylformamide (30 mL) as the solvent in a 250 mL two-neck round bottom flask fitted with a reflux condenser, heating bath and a nitrogen bubbler. One hundred to two hundred ppm of hydroquinone is used during the reaction to avoid unexpected polymerization. The temperature of the heating bath is maintained at 55° C. during the reaction. After 12 hours, N,N-dimethylformamide is removed under reduced pressure using a rotary evaporator (55° C., 8 mbar). The crude material is dissolved in 50 mL ethyl acetate and washed with brine solution (15 mL×3). The ethyl acetate layer is separated, dried over anhydrous Na$_2$SO$_4$, decolorized from activated charcoal, and the solvent is removed under reduced pressure in a rotary evaporator. The final product is obtained in quantitative yield (18 grams, isolated yield).

The final product is well characterized by infrared spectroscopy, multinuclear NMR ($^1$H, $^{13}$C, $^{29}$Si) spectroscopy.

The proton and silicon NMR results of the final monomer are: $^1$H-NMR, 400 MHz, CDCl$_3$ (ppm): 0.03 to 0.12 (br. m, 21H, CH$_3$Si—), 0.2 to 0.3 (m, 1H, Si—CH$_2$), 0.52 to 0.60 (m, 1H, Si—CH$_2$—), 0.92 (d, J=8 Hz, 3H, —CH$_3$), 1.8 to 1.9 (m, 1H, —CH(R)), 1.97 (br. S, 3H, =C(CH$_3$)), 3.06 to 3.1 (m, 1H, R—CH$_2$CH$_2$O—), 3.22 to 3.35 (m, 1H, R—CH$_2$CH$_2$O—), 3.4 to 3.8 (m, 34H, —(CH$_2$CH$_2$O)$_n$—), 4.08 to 4.18 (m, 2H, NH—CH$_2$COO—), 4.27 to 4.37 (m, 2H, OOC—CH$_2$) 5.37 (br. S, 1H, =CH$_2$), 5.76 (br. S, 1H, =CH$_2$), 6.46 (br. S, 1H, —NH—CO). $^{29}$Si-NMR, 79.51 MHz, CDCl$_3$ (ppm): -22.3 (—OSi—(CH$_3$)(EO)), 6.8 (—OSi(CH$_3$)$_3$).

General Examples of Hydrogel Films

Different hydrogel films are prepared from the formulations (Formulas 1-9) derived from the materials given in Examples 1, 2, 3, 4, 5 and 7 along with organic co-monomers such as 2-hydroxyethyl methacrylate (HEMA), N,N-dimethylacrylamide (DMA), N-vinylpyrrolidone (NVP), methacryloxypropyl tris(trimethylsiloxy)silane (TRIS), trisiloxane grafted methallylpolyether methacrylate with 4 moles of ethyleneoxide (Example 6), and optionally with cross-linkers such as ethyleneglycoldimethacrylate (EGDMA). 2-hydroxy,2-methyl propiophenone (HMPP) or Irgacure 819 is used as a UV initiator. All the films are cured using 1 weight percent of the initiator and cured with a 365 nm lamp for 5-60 seconds in transparent molds made up of glass or poly(propylene) or polyester sheets. The curing was faster when glass was used as molds (2-3 seconds). Details of the formulations and the properties of the hydrogel films are summarized in Table 1. The curing properties of silicone acrylamides (Example 1-5 and 7) of the current invention compared to known silicone acrylates (Example 6) are summarized in Table 2.

TABLE 1

Hydrogel Formulations and Their Properties

| Ingredients (%) | Formula 1 | Formula 2 | Formula 3 | Formula 4 | Formula 5 | Formula 6 | Formula 7 | Formula 8 | Formula 9 |
|---|---|---|---|---|---|---|---|---|---|
| Example 1 | | 39.4 | | | | | 49.3 | | |
| Example 2 | | | | | 49.3 | | | | |
| Example 3 | | | 39.4 | | | | | | |
| Example 4 | | | | | | | | | |
| Example 5 | | | | 39.4 | | | | | 49.3 |
| Example 6 | 39.4 | | | | | | | 49.3 | |

TABLE 1-continued

Hydrogel Formulations and Their Properties

| Ingredients (%) | Formula 1 | Formula 2 | Formula 3 | Formula 4 | Formula 5 | Formula 6 | Formula 7 | Formula 8 | Formula 9 |
|---|---|---|---|---|---|---|---|---|---|
| Example 7 | | | | | | | | | 49.3 |
| TRIS | 9.9 | 9.9 | 9.9 | 9.9 | | | | | |
| DMA | 19.7 | 19.7 | 19.7 | 19.7 | 24.6 | 24.6 | 24.6 | 24.6 | 24.6 |
| HEMA | 24.6 | 24.6 | 24.6 | 24.6 | 19.7 | 19.7 | 19.7 | 19.7 | 19.7 |
| NVP | 4.9 | 4.9 | 4.9 | 4.9 | 4.9 | 4.9 | 4.9 | 4.9 | 4.9 |
| EGDMA | 0.5 | 0.5 | 0.5 | 0.5 | 0.5 | 0.5 | 0.5 | 0.5 | 0.5 |
| HMPP | 1 | 1 | 1 | 1 | 1 | 1 | 1 | 1 | 1 |
| Water Uptake (wt. %) | 34 ± 2 | 44 ± 2 | 45 ± 2 | 35 ± 2 | 52 ± 2 | 50 ± 2 | 45 ± 2 | 54 ± 2 | 62 ± 2 |
| Percent Transmission (1 mm thickness) | >94 | >94 | >94 | >95 | >95 | >94 | >95 | >94 | >95 |
| Modulus (MPa) | 0.6 ± 0.1 | 0.8 ± 0.1 | 0.9 ± 0.1 | 1 ± 0.1 | 0.7 ± 0.2 | 0.8 ± 0.2 | 0.5 ± 0.1 | 0.7 ± 0.1 | 0.6 ± 0.2 |

TABLE 2

Curing properties of 97 wt % silicone hydrogel formulation with 1 wt % EGDMA cross-linker and 2 wt % HMPP initiator. The curing was done using 365 nm UV-light in a Dymax UV-irradiation chamber. The viscosity of the formulation was analyzed on a RS600 Haake Rheometer (23° C., Sensor 20 mm/1° cone-plate). Example 1 of current invention showed excellent curing properties compared to Example 6 known in art.

| | Viscosity/Pa · s (Seen during the cure) | | | | |
|---|---|---|---|---|---|
| Cure time/s | 0 | 10 | 25 | 50 | 90 |
| Example 1 | 0.2 | 150 | >10$^6$ (film) | >10$^6$ (film) | >10$^6$ (film) |
| Example 6 | 0.035 | 0.04 | 0.15 | 0.7 | 0.9 |

While the invention has been described with reference to a various embodiment, those skilled in the art will understand that various changes can be made and equivalents can be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

What is claimed is:

1. A hydrogel composition comprising at least one silicone acrylamide monomer, the silicone acrylamide monomer having a formula as set forth in Formulas (I) or (II) below:

(I)

(II)

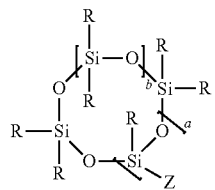

wherein a is 1 to 50; b is 0 to 100; each R is independently selected from the group comprising of a monovalent aliphatic, cycloaliphatic, or aromatic hydrocarbon group of 1 to about 10 carbons, a halogenated hydrocarbon group of 1 to about 10 carbons, and a radical comprising 1 to about 50 silicon atoms, or a trialkylsilyloxy group and Z is a polyether moiety having a non-isomerizable hydrosilylation effective terminal olefinic residue having Formula (III):

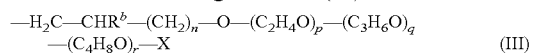
(III)

wherein n is 1 to about 20; p and q are independently 0 to about 100; r is 0 to about 50, and (p+q+r) is greater than 0; Rb is an alkyl group having from 1 to about 4 carbon atoms, X is a vinyl group, an N-vinyl derivative, even an N-vinyl-pyrrolidone derivative, or a polyether-capping group having Formula (IVb):

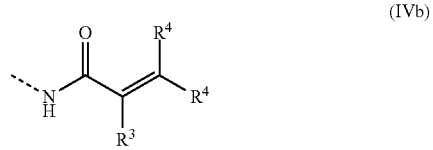
(IVb)

wherein $R^3$ and $R^4$ independently are either hydrogen or a substituted or unsubstituted saturated monovalent hydrocarbon group of 1 to about 20 carbons or —COOH or —CH$_2$—COOH.

2. The hydrogel composition of claim 1, wherein the silicone acrylamide monomer comprises (a) a reaction of (i) silicone-containing compound having Formula (V):

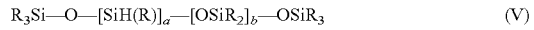
(V)

wherein a is 1 to 50; b is 0 to 100; each R is independently selected from the group consisting of a monovalent aliphatic, cycloaliphatic, or aromatic hydrocarbon group of 1 to about 10 carbons, and halogenated hydrocarbon groups of 1 to about 10 carbons; with (ii) a polyether having at least one end terminated with hydroxyl, a halogen, or an epoxy, and the other end terminated with a branched alkene having Formula (VI):

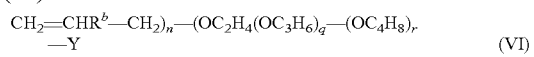
(VI)

wherein n is 1 to about 20, p and q are 0 to about 100; r is 0 to about 50; Rb is an alkyl group having from 1 to about 4 carbon atoms, Y is —OH, a halogen, an epoxy or an amine, the reaction of (i) and (ii) being conducted in the presence of a catalyst to produce a polyether siloxane, and (b) reacting the polyether siloxane with an acryl compound having Formula (VII):

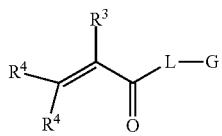
(VII)

wherein L is an optional linker group chosen from a monovalent aliphatic, a cycloaliphatic, or an aromatic hydrocarbon radical of 1 to about 16 carbons, which can optionally contain a heteroatom or a halogen; G is a halogen or —OH and its organic or inorganic salts, and $R^3$ and $R^4$ independently are either hydrogen or a hydrocarbon group of 1 to about 10 carbons or —COOH or —CH$_2$—COOH to produce said silicone acrylamide monomer.

3. The hydrogel composition of claim 2, wherein L is a moiety having Formula:

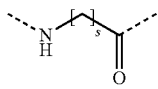

wherein s is an integer selected from 0 to about 15.

4. The hydrogel composition of claim 1, comprising the silicone acrylamide monomer is of the formula:

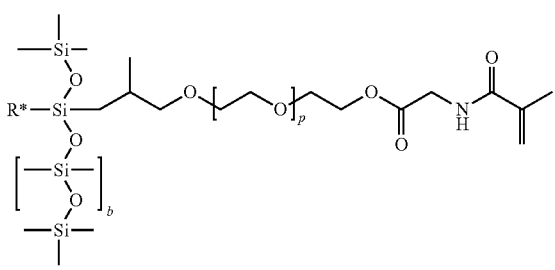

wherein R* is a trialkylsilyloxy group or a methyl group, p is 1 to about 50, and b is 0 to about 100.

5. The hydrogel composition of claim 1, comprising the silicone acrylamide monomer of the formula:

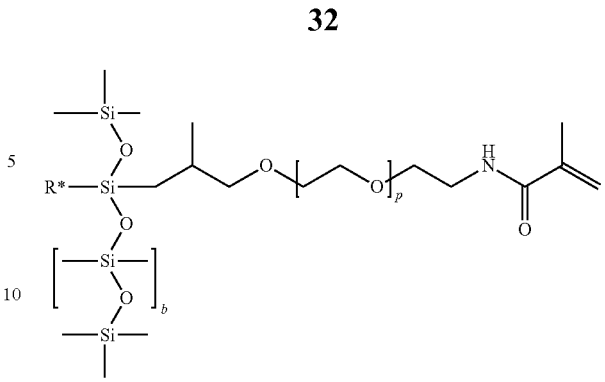

wherein R* is a trialkylsilyloxy group or a methyl group, p is 1 to about 50, and b is 0 to about 100.

6. The hydrogel composition of claim 1, comprising the silicone acrylamide monomer of the formula:

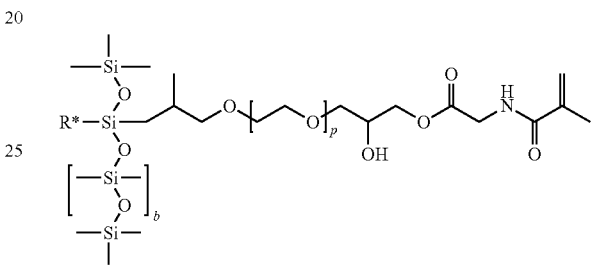

wherein R* is a trialkylsilyloxy group or a methyl group, p is 1 to about 50 and b is 0 to about 100.

7. The hydrogel composition of claim 1, comprising the silicone acrylamide monomer of the formula:

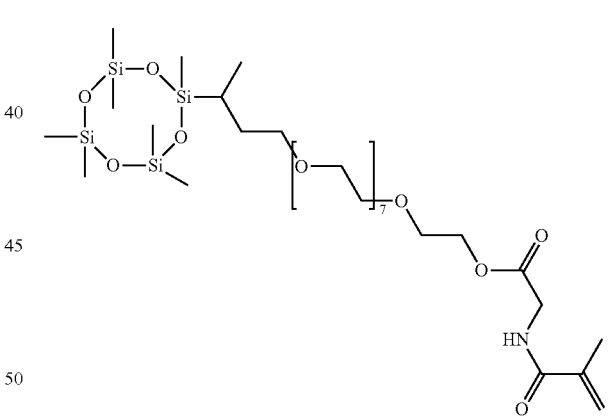

wherein R* is a trialkylsilyloxy group or a methyl group, p is 1 to about 50, and b is 0 to about 100.

8. The hydrogel of claim 1, wherein the co-monomer is chosen from a silicone-containing monomer, an organic based monomer, or a combination of two or more thereof.

9. The hydrogel of claim 1, wherein the hydrogel further comprises a co-monomer chosen from a vinylic monomer, an allylic monomer, an acrylide monomer, an acrylic monomer, or a combination of two or more thereof.

10. The hydrogel of claim 8, wherein the vinylic monomer is chosen from N-vinyl-pyrrolidone, N-vinyl-caprolactam, N-vinyl-acetamide, N-vinyl-formamide, N-vinyl-isopropyl-amide, vinyl benzene, vinyl naphthalene, vinyl pyridine, vinyl alcohol, a vinyl containing silicones, or a combination of two or more thereof.

11. The hydrogel of claim 8, wherein the vinyl, allyl, or acrylide, or acrylic monomer is chosen from 3-[Tris(trimethylsiloxy)silyl]propyl methacrylate; methyl-di(trimethylsiloxy)-silyl propyl glycerol methacrylate; 3-(trimethylsilyl) propyl vinyl carbonate; 3-(vinyloxycarbonylthio)propyl-[tris(trimethylsiloxy)silane]; 3-[tris(tri-methylsiloxy)silyl] propyl vinyl carbamate; 3-[tris(trimethylsiloxy)silyl]propyl allyl carbamate; 3-[tris(trimethylsiloxy)silyl]propyl vinyl carbonate, or a combination of two or more thereof.

12. The hydrogel of claim 8, wherein the acrylic organic monomer is chosen from 2-hydroxy-ethyl-methacrylate (HEMA), 2-hydroxy-ethyl-acrylate (HEA), hydroxyl propyl methacrylate, trimethylammonium 2-hydroxy propyl methacrylate hydrochloride, dimethylaminoethyl methacrylate, glycerol methacrylate, N,N-dimethyl acrylamide, N-isopropylacrylamide, acrylamide, methacrylamide, acrylic acid, methacrylic acid, an acrylated hydrophilic or hydrophobic organo-silicone, or a combination of two or more thereof.

13. The hydrogel of claim 1, further comprising a crosslinker chosen from ethylene glycol dimethacrylate, trimethyloylpropane trimethacrylate, diethyleneglycol dimethacrylate, bisphenol A dimethacrylate, diglycidyl bisphenol A dimethacrylate, dimethacrylate-terminated polyethylene glycol, a reactive linear or pendant polyether modified silicone, or a combination of two or more thereof.

14. The hydrogel composition of claim 1, wherein the composition further comprises a thermal or a photo initiator chosen from 2,2'-azobis (2,4-dimethylpentanenitrile), 2,2'-azobis (2-methylpropanenitrile), 2,2'-azobis (2-methylbutanenitrile), benzoyl peroxide, benzoin methyl ether, diethoxyacetophenone, a benzoylphosphine oxide, 2-hydroxy-2-methyl propiophenone (HMPP), 1-hydroxycyclohexyl phenyl ketone, a Darocur-type initiator, an Irgacure-type initiator or a combination of two or more thereof.

15. The hydrogel composition of claim 1, wherein, the hydrogel composition cures to a self-standing film in time of about 10 seconds or less using 365 nm light with an intensity of 105 mW/cm$^2$.

16. A contact lens comprising the hydrogel film of claim 1.

17. The contact lens according to claim 16 comprising a limited extraction protocol that further comprises a green or aqueous solvents chosen from water, an organic or inorganic salt solutions, a buffer, an emulsion, a commercial lens cleaning solution, or an ophthalmically compatible solvent in the temperature range of 15-125° C. for extraction.

18. The composition according of claim 1, wherein the composition is a film forming additive in a textile, paper, leather, personal care, health care, home care, coating, painting, or seed treatment formulations.

19. The hydrogel composition of claim 4, wherein p is from 2 to 15.

20. The hydrogel composition of claim 5, wherein p is from 2 to 15.

21. The hydrogel composition of claim 6, wherein p is from 2 to 15.

22. The hydrogel composition of claim 7, wherein p is from 2 to 15.

\* \* \* \* \*